: US 7,731,975 B2
(12) United States Patent
Grogan et al.

(10) Patent No.: US 7,731,975 B2
(45) Date of Patent: Jun. 8, 2010

(54) CHIMERIC FILOVIRUS GLYCOPROTEIN

(75) Inventors: Case C. Grogan, Gaithersburg, MD (US); Michael C. Hevey, Frederick, MD (US); Alan L. Schmaljohn, Frederick, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1892 days.

(21) Appl. No.: 10/066,506

(22) Filed: Jan. 31, 2002

(65) Prior Publication Data

US 2003/0108560 A1    Jun. 12, 2003

Related U.S. Application Data

(60) Provisional application No. 60/267,522, filed on Jan. 31, 2001.

(51) Int. Cl.
 *A61K 39/295* (2006.01)
 *A61K 39/12* (2006.01)
 *C12N 15/00* (2006.01)
(52) U.S. Cl. ............... 424/202.1; 424/204.1; 435/320.1
(58) Field of Classification Search .................. 435/5, 435/6, 69.7, 339; 330/387.3; 424/192.1, 424/186.1, 202.1, 204.1; 536/23.72
 See application file for complete search history.

(56) References Cited

FOREIGN PATENT DOCUMENTS

WO    WO0000616    1/2000
WO    WO0000617    1/2000

OTHER PUBLICATIONS

Partidos, C., et al., 1992(a), "The effect of orientation of epitopes on the immunogenicity of chimeric synthetic peptides representing measles virus protein sequences.", Mol. Immunol. 29(5):651-8 (abstract provided).*

Partidos, C., et al., 1992(b), "The effects of a flanking sequence on the immune response to a B and a T cell epitope from the fusion protein of measles virus.", J. Gen. Virol. 73(8):1987-94 (abstract provided).*

Janssen, R., et al., 1994, "Influence of amino acids of a carrier protein flanking an inserted T cell determinant on T cell stimulation.", Internat. Immunol. 6(8):1187-1193 (abstract provided).*

Eisenlohr, L. C., et al., 1992, "Flanking sequences influence the presentation of an endogenously synthesized peptide to cytotoxic T lymphocytes.", J. Exp. Med. 175(2):481-7 (abstract provided).*

Ayato, T., et al., 2003, "Identification of protective epitopes on Ebola virus glycoprotein at the single amino acid level by using recombinant vesicular stomatitis viruses.", J. Virol. 77(2):1069-74 (abstract provided).*

London, S. D. et al., 1992. Infectious enveloped RNA virus antigenic chimeras. PNAS, 89, 207-211.

Klenk Hans Dieter et al., 2001. Symposium on Marburg and Ebola viruses. Virus Research 80, 117-123.

* cited by examiner

*Primary Examiner*—J. S. Parkin
(74) *Attorney, Agent, or Firm*—Elizabeth Arwine

(57) ABSTRACT

Chimeric GP molecules were constructed which contain portions of both the EBOV and MBGV GP proteins by swapping the subunits between EBOV and MBGV. The chimeric molecules were cloned into an alphavirus replicon which offers the advantage of high protein expression levels in mammalian cells and is a proven vaccine vector. These chimeric molecules fully protected guinea pigs from MBGV challenge, and conversely protected the animals from EBOV challenge. These results indicate that a protective epitope resides within the GP2 subunit of the MBGV GP protein and at least partially within the GP2 subunit of the EBOV GP protein. Additionally these results show that a construction of a single-component bivalent vaccine protective in guinea pigs is achievable.

37 Claims, 13 Drawing Sheets

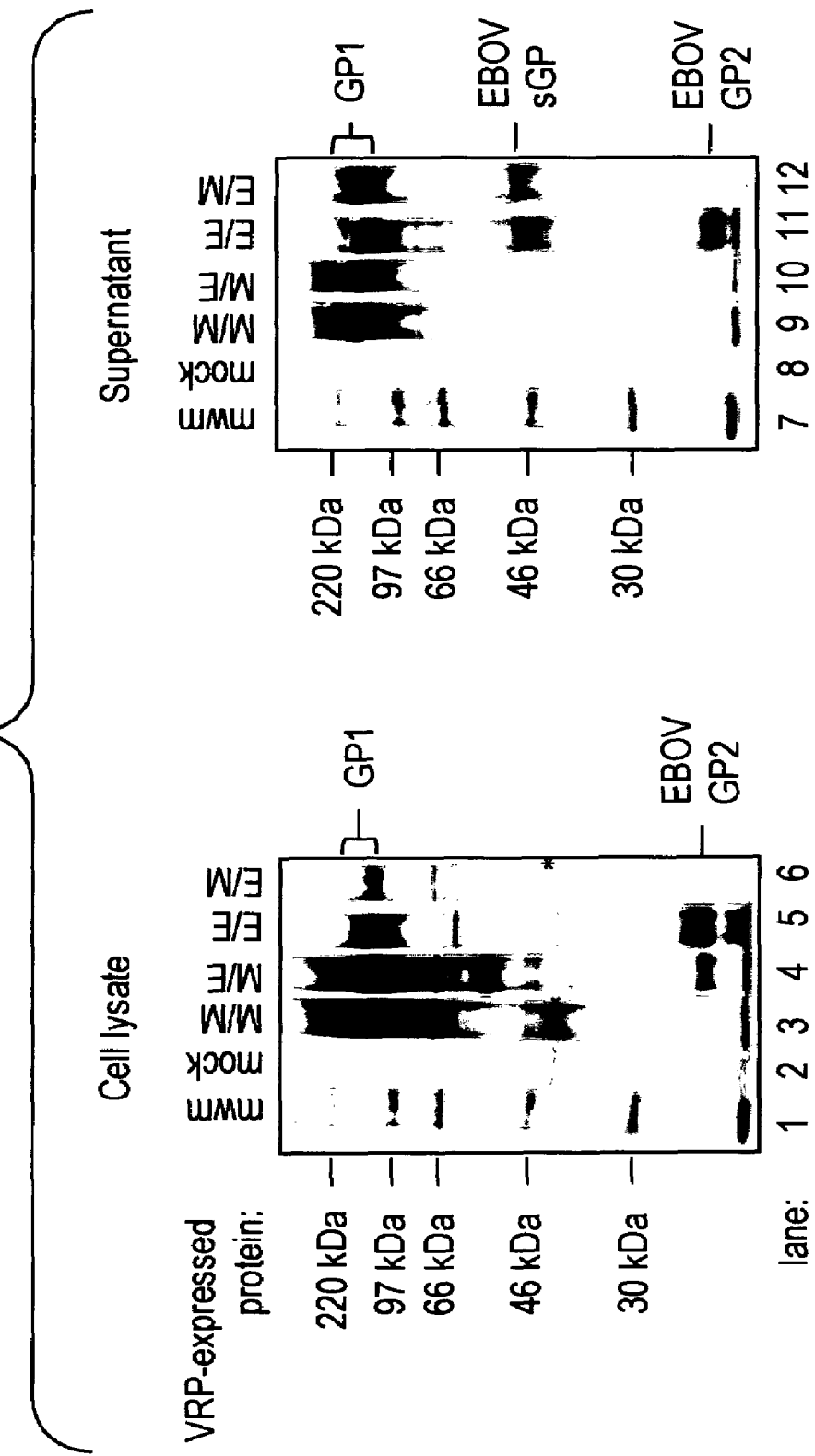

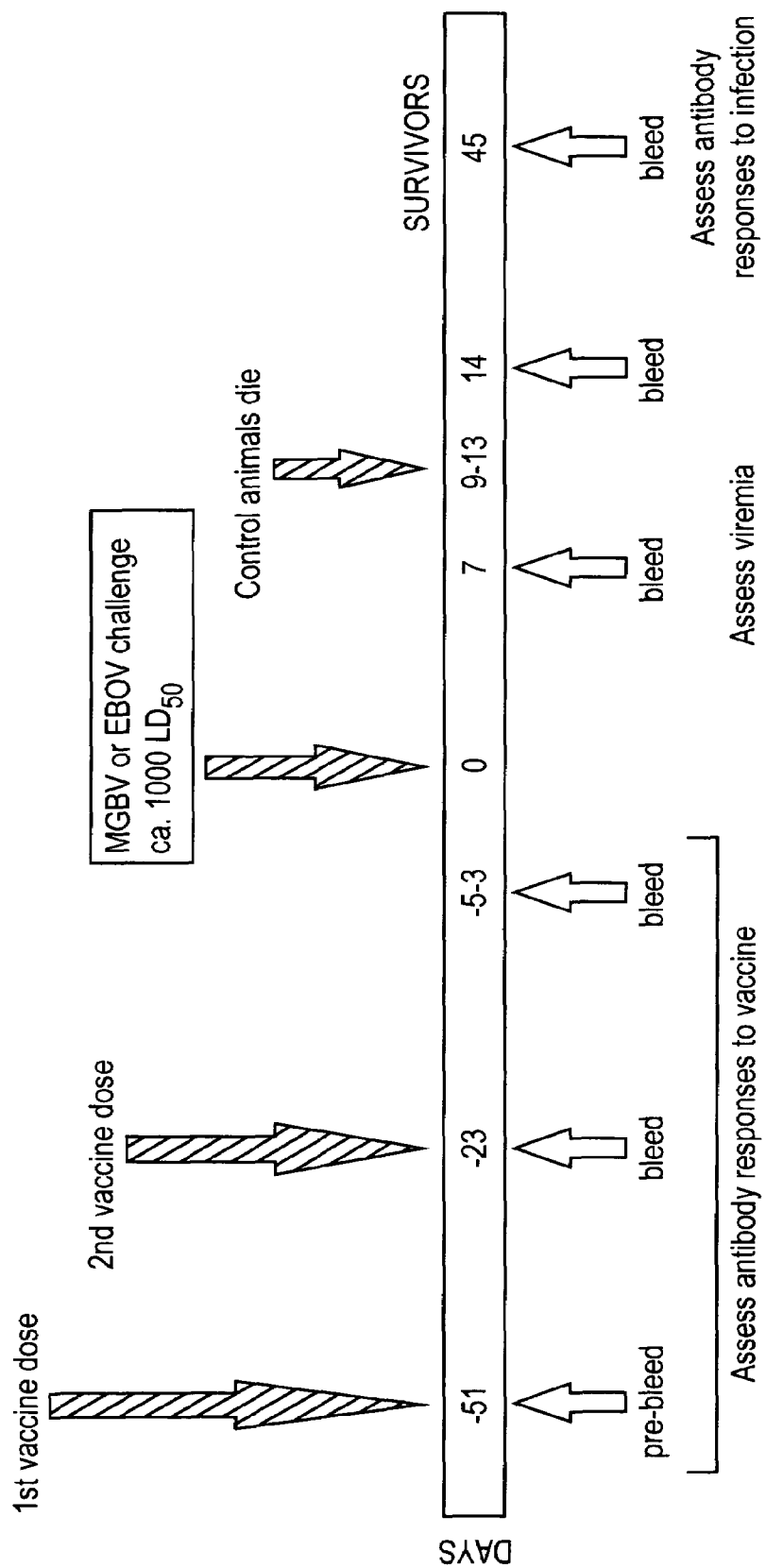

FIG. 6B
EBOV challenge

FIG. 7A
MBGV Challenge

| VRP-Delivered Antigen | Serum Viremia (log₁₀ PFU/ml) | Ratio |
|---|---|---|
| M/M | — | 0/5 |
| M/E | — | 0/6 |
| E/E | ~4.5 | 9/9 |
| E/M | ~2.7 | 3/6 |
| LassaNP | ~3.4 | 4/6 |

FIG. 7B
EBOV Challenge

| VRP-Delivered Antigen | Serum Viremia (log₁₀ PFU/ml) |
|---|---|
| M/M | 9/9 (~3.2) |
| M/E | 1/9 (~3.2) |
| E/E | 0/9 |
| E/M | 0/9 |
| LassaNP | 9/9 (~5.0) |

FIG. 8A
E/M Sera, MBGV Antigen

□ Native
▨ Detergent Disrupted

---- Lower limit of assay detection

Y-axis: $\text{Log}_{10}$ Elisa Titer (0.5 to 5.5)
X-axis: Challenge (Pre-MBGV, Post-MBGV, Pre-EBOV, Post-EBOV)

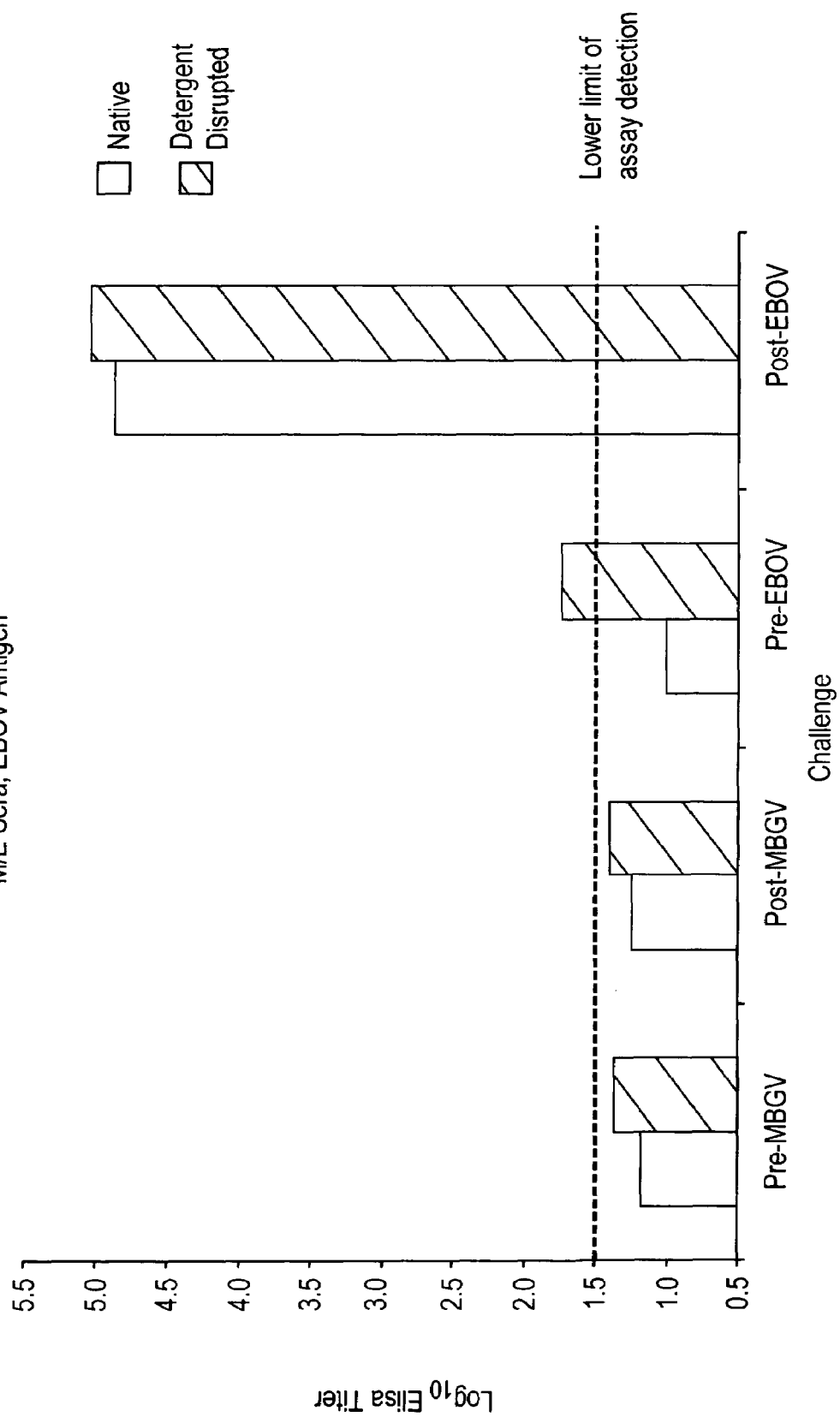

FIG. 9

| | Sera: | α-E/M | α-EBOV | α-M/E | α-MBGV | |
|---|---|---|---|---|---|---|
| MBGV GP1 | | | | | | 200 kDa |
| | | | | | | 116 kDa |
| | | | | | | 97 kDa |
| | | | | | | 66 kDa |
| | | | | | | 45 kDa |
| MBGV GP2 | | | | | | 31 kDa |
| | | | | | | 21 kDa |
| | lane: | 1 | 2 | 3 | 4 | |

CHIMERIC FILOVIRUS GLYCOPROTEIN

This application claims the benefit of an earlier filed application Ser. No. 60/267,522 filed on Jan. 31, 2001.

INTRODUCTION

Marburg virus (MBGV) was first recognized in 1967, when an outbreak of hemorrhagic fever in humans occurred in Germany and Yugoslavia, after the importation of infected monkeys from Uganda (Martini and Siegert, 1971, *Marburg Virus Disease*. Berlin: Springer-Verlag; Smith et al., 1982, *Lancet* 1, 816-820). Thirty-one cases of MBGV hemorrhagic fever were identified that resulted in seven deaths. The filamentous morphology of the virus was later recognized to be characteristic, not only of additional MBGV isolates, but also of Ebola virus (EBOV) (Johnson et al., 1977, *J. Virol.* 71, 3031-3038; Smith et al., 1982, *Lancet* 1, 816-820; Pattyn et al., 1977, *Lancet* 1, 573-574). MBGV and EBOV are now known to be distinctly different lineages in the family Filoviridae, within the viral order Mononegavirales (Kiley et al., 1982, *Intervirology* 18, 24-32; Feldmann and Klenk, 1996, *Adv. Virus Res.* 47, 1-52).

Few natural outbreaks of MBGV and EBOV disease have been recognized, and all proved self-limiting, with no more than two cycles of human-to-human transmission. However, the actual risks posed by MBGV and EBOV to global health cannot be assessed because factors which restrict the virus to its unidentified ecological niche in eastern Africa, and those that limit its transmissibility, remain unknown (Feldmann and Klenk, 1996, supra). Concern about MBGV is further heightened by its known stability and infectivity in aerosol form (Belanov et al., 1996, *Vopr. Virusol.* 41, 32-34; Frolov and Gusev Iu, 1996, *Vopr. Virusol.* 41, 275-277). Thus, laboratory research on MBGV and EBOV is necessarily performed at the highest level of biocontainment. To minimize future risk, our primary interest has been the identification of appropriate antigens and vaccine strategies that can provide immunity to MBGV and EBOV.

The filovirus genome is composed of a non-segmented, negative sence, single stranded RNA of approximately 19 Kb. The open reading frames of the genome encode seven viral proteins: GP, the surface viral glycoprotein; NP, the major nucleocapsid protein; VP30, a minor nucleocapsid protein; VP35, a nonstructural protein; VP40 and VP24, internal membrane associated proteins; and L, the viral RNA-dependent RNA polymerase. In addition, Ebola virus encodes and 8th protein termed sGP (secreted glycoprotein). This protein is transcribed from the same open reading frame as full length GP. The function of sGP is unknown.

Vaccination with Marburg or Ebola GP protects from disease and death in rodent models of infection. MBGV GP delivered by Venezuelan equine encephalitis (VEE) virus replicon protected guinea pigs against infection by a homologous strain of Marburg virus (Musoke) (Hevey et al, 1998, *Virology* 251: 28-37). Similarly, vaccination with EBOV GP delivered by VEE replicon or DNA vaccination also elicited protective immunity in rodent models of Ebola virus infection (Pushko et al., 200, *Vaccine* 19, 142-153; VanderZanden et al., 1998, *Virology* 246, 134-144). However, when guinea pigs vaccinated with VEE replicons expressing MBGV (strain Musoke) GP were challenged with a heterologous strain of MBGV (Ravn), complete protection was not observed, indicating that genetic variability among filoviruses may present an obstacle in obtaining a broadly cross reactive vaccine. Not surprisingly, vaccination with MBGV GP does not confer protection to challenge with Ebola virus, and vice versa. The GP proteins of MBGV Musoke and MBGV Ravn are 78% identical, compared to only 27% identity between MBGV Musoke and Ebola strain Zaire, indicating that genetic variability among filoviruses may present an obstacle in obtaining a broadly cross reactive vaccine.

Therefore, there is a need for an efficacious broadly cross-reactive vaccine able to protect against multiple filovirus strains.

SUMMARY OF THE INVENTION

The present invention satisfies the need discussed above. The present invention relates to a method and composition for use in inducing an immune response which is protective against infection with different filoviruses. More specifically, the present invention describes a single-component bivalent vaccine protective against both Ebola and Marburg viruses which is cost-effective and efficient to produce, develop and test. The present invention also embodies the production of similar vaccines, whether, bivalent, trivalent, or multivalent able to elicit a protective immune response to multiple filovirus agents in a single-component. Two strains of filoviruses were chosen, Marburg Musoke and Ebola Zaire which are the most divergent of all the filoviruses. If protection against both of these particular most-divergent strains is achieved in a single chimeric GP, chimeras made up of any other filovirus strains would be expected to also be cross-protective.

In order to elicit an immune response to both Marburg and Ebola, a chimeric glycoprotein was constructed using GP from each of the two viruses. Two forms of the glycoprotein are produced by transcription of the Ebola virus GP gene. Transcription and translation of the genomic copy of the GP gene results in a secreted, truncated form of the membrane-bound GP, termed sGP. The transmembrane GP protein is encoded in two open reading frames (ORFs) via a co-transcriptional editing mechanism whereby the viral polymerase inserts a non-templated adenosine residue at a specific editing site consisting of a run of seven adenosine residues (Volchkov et al, 1995, *Virology* 214, 421-430; Sanchez et al., 1996, *J. Gen. Virol.* 73, 347-357). Translation of the resulting mRNA has a frameshift at the editing site, such that sGP is identical to GP up to the editing site (aa295) but divergent thereafter, with a unique 69aa carboxy-terminus. MBGV, in contrast, encodes a single transmembrane GP protein using a single ORF (Will et al., 1993, *J. Virol.* 76, 1203-1210). The GP proteins of MBGV, (strain Musoke, 681aa, Genbank accession #Z12132 S55429, Feldmann et al., 1992, *Virus Res.* 24, 1-19) and EBOV (strain Zaire, strain Mayinga, 676aa, Genbank accession #U23187) are 27% identical and 39% homologous. Sequence differences between the two GPs are clustered in a hypervariable region spanning the middle third of the protein, while the N and C termini are more conserved. Both MBGV and EBOV GPs are highly glycosylated and are post-translationally cleaved by a host-cell furin-like protease into two disulfide-linked subunits, termed GP1 and GP2 (FIG. 1) (Volchkov et al., 2000, *Virology* 286, 1-6; Volchkov et al., 1998, *Proc. Natl. Acad. Sci. USA* 95, 5762-5767; Becker et al., 1996, *Virology* 225, 145-155). The transmembrane anchor is located within the GP2 subunit, while the majority of the glycosylation sites are located within GP1 (Feldmann et al., 1999, *Arch. Virol.* 15, 159-169).

The purpose of our chimeric proteins was to construct a full-length GP (normally consisting of two subunits, GP1 and GP2) containing a subunit from EBOV with the other subunit from MBGV. There was no duplication or deletion of amino acid sequence from the heterologous virus GP in the portions that were cloned together, in order to preserve as much as possible the tertiary structure of the molecule. In other words, the chimeras still have one, and only one, full GP1 subunit and only one full GP2 subunit, as the wild-type EBOV and MBGV GPs do. This was done in order to study the biologic and immunologic properties of the resulting chimera protein in the context of an authentic GP (with respect to 3D or tertiary structure), specifically if any particular function could be attributed to one of the two subunits. This has never been done before for filoviruses, or for any other virus surface glycoprotein. Chimeric GP proteins were constructed by swapping the subunits between EBOV and MBGV. The furin cleavage site of each of these molecules was selected as the junction site for this initial set of chimeras. Several problems were presented by this design.

First, the GP1 and GP2 subunits of wild-type MBGV and EBOV are post-translationally cleaved by a host-cell protease. The cleavage sites for the two proteins are not identical, so putting the cleavage site of one virus in the context of foreign downstream GP2 sequence could potentially disrupt cleavage. Additionally, it would be unknown whether the chimeric subunits, even if cleaved, would still be disulfide bonded as are the wild-type homologous GP1 and GP2 subunits.

Second, the putative structure of GP includes a large, globular, glycosylated GP1 subunit that is most distal to the surface of the membrane, and a smaller GP2 subunit that anchors the GP to the membrane. It is thought that the GP1 subunit is seen by the host immune system, and "shields" the GP2 subunit from being recognized or even being accessible to the host immune system. This is supported by the fact that the highly variable region of GP is located entirely in the GP1 subunit, and regions of variability are thought to correlate with antigenically accessible regions. Therefore one would not expect a chimeric protein with the GP2 subunit from MBGV to protect from MBGV challenge, and conversely one would not expect a chimeric protein with EBOV GP2 to protect from EBOV challenge. One would have predicted that the GP2 subunits are just too small and too hidden to be antigenic.

To begin exploring the possibility of generating a broadly cross-relative vaccine, chimeric EBOV/MBGV GP molecules were constructed in a Venezuelan equine encephalitis (VEE) replicon vector for expression in mammalian cells.

In this study a vaccine delivery system based on a virus replicon was used to identify candidate protective antigens in nonhuman primates. In this vaccine strategy, a gene coding for a protein of interest is cloned in place of the VEE virus structural genes; the result is a self-replicating RNA molecule that encodes its own replicase and transcriptase functions, and in addition makes abundant quantities of mRNA encoding the foreign protein. When replicon RNA is transfected into eukaryotic cells along with two helper RNAs that express the VEE structural proteins (glycoproteins and nucleocapsid), the replicon RNA is packaged into VEE virus-like particles by the VEE virus structural proteins, which are provided in trans. Since the helper RNAs lack packaging signals necessary for further propagation, the resulting VEE replicon particles (VRPs) which are produced are infectious for one cycle but are defective thereafter. Upon infection of an individual cell with a VRP, an abortive infection occurs in which the infected cell produces the protein of interest in abundance, is ultimately killed by the infection, but does not produce any viral progeny (Pushko et al., 1997, *Virology* 239, 389-401). The VEE replicon is described in greater detail in U.S. Pat. No. 5,792,462 issued to Johnston et al. on Aug. 11, 1998.

Results shown here demonstrate that both chimeric GP molecules tested, E/M and M/E, protect guinea pigs against both EBOV and MBGV infection.

Therefore, it is one object of the present invention to provide a chimeric protein comprising GP1 or a portion thereof from one filovirus and GP2 or a portion thereof from another filovirus to produce a chimeric GP protein. By portion, is meant a part of the protein of at least 1 amino acid which is immunologically identifiable with the protein. Different portions of GP1 and GP2 can be used to make up the complete GP chimeric protein. When the chimeric protein is used for a vaccine, the portions of GP1 and GP2 are preferably immunogenic, or elicit an immune response in a subject against the filoviruses from which these portions were derived. A multivalent vaccine against more than two filoviruses can be designed using immunogenic portions of GP1 and GP2 from more than two filoviruses to produce the chimeric GP protein.

It is another object of the invention to provide a DNA fragment encoding any of the chimeric GP proteins EBOV-GP1 with MBGV-GP2 (E/M), MBGV-GP1 with EBOV-GP2 (M/E), EBOV-GP1 with EBOV-GP2 (E/E), MBGV-GP1 with MBGV-GP2 (M/M), MBGV-RVN GP1 with MBGV-MUS GP2 (Rvn/Mus), MBGV-MUS GP1/MBGV-RVN GP2 (Mus/Rvn) and MBGV-RVN GP1/MBGV-RVN GP2 (Rvn/Rvn) described below.

It is yet another object of the present invention to provide the above DNA fragment as part of a recombinant vector. For example, the vector is a VEE virus replicon vector comprising a VEE virus replicon and a DNA fragments as described above.

It is another object of the present invention to provide a self replicating RNA comprising the VEE virus replicon and any of the EBOV-GP1 with MBGV-GP2 (E/M), MBGV-GP1 with EBOV-GP2 (M/E), EBOV-GP1 with EBOV-GP2 (E/E), MBGV-GP1 with MBGV-GP2 (M/M), MBGV-RVN GP1 with MBGV-MUS GP2 (Rvn/Mus), MBGV-MUS GP1/MBGV-RVN GP2 (Mus/Rvn) and MBGV-RVN GP1/MBGV-RVN GP2 (Rvn/Rvn) described above.

It is another object of the present invention to provide infectious VEE virus replicon particles produced from the VEE virus replicon RNA described above.

It is further an object of the invention to provide an immunological composition for the protection of mammals against filovirus infection such as MBGV and EBOV infection comprising VEE virus replicon particles containing nucleic acids encoding any portion of the filovirus GP for which protection is desired such as MBGV GP and EBOV GP.

It if yet another object of the present invention to provide an immunological composition for the protection of mammals against filovirus infection comprising VEE virus replicon particles containing nucleic acids encoding a chimeric glycoprotein comprised of any portion of a glycoprotein from any number of filoviruses for which protection against infection is desired. In order to define smaller regions of GP essential for protection, smaller and smaller portions of GP may be swapped between EBOV and MBGV and tested for protection. An understanding of the protective epitopes and GP structure would allow the design of a chimera that contains portions of multiple filovirus GPs resulting in a multivalent vaccine molecule.

BRIEF DESCRIPTION OF THE DRAWINGS

These and other features, aspects, and advantages of the present invention will become better understood with reference to the following description and appended claims, and accompanying drawings where:

FIG. 4. Immunoprecipitation of VRP-expressed proteins. Convalescent sera from MBGV infected guinea pigs was used to immunoprecipitate M/M and M/E protein, and convalescent sera from EBOV infected guinea pigs was used to immunoprecipitate E/E and E/M protein from the cell lysate (lanes 1-6) or supernatant (lanes 7-12) of $^{35}$S-radiolabeled VRP-infected Vero cells. MBGV GP1 is present in both cell lysate and supernatant from M/M and M/E infected cultures (lanes 3-4 and 9-10), and EBOV GP1 is present in both cell lysate and supernatant from E/E and E/M infected cultures (lanes 5-6 and 11-12). EBOV GP2 is present in the lysate of M/E and E/E infected cells (Lanes 4-5). MBGV GP2 was difficult to detect in lanes 3 or 6; * marks the site of a heterogeneous population of labeled products, the expected size of MBGV-GP2, visible upon overexposure of the gel. Mock infected cell lysate non-specifically bound a protein just under 46 kDa (lane 2), but upon overexposure this discrete band was distinct from that seen in lanes 3 and 6. No proteins nonspecifically bound from mock-infected cell supernatants (lane 8). For reference a molecular weight marker (mwm) is shown in lanes 1 and 7.

FIG. 5. Guinea Pig Vaccination Schedule. The numbers in the yellow box refer to days pre- and post-virus challenge, set as day 0. Animals were vaccinated twice, 28 days apart, and challenged ~28 days after the second vaccine dose. Animals were anesthetized and bled at the time of each vaccination and before challenge to asses antibody titers. Post-challenge bleeds at days 7 and 14 were used to determine viremia.

FIG. 7. Viremias post MBGV (A) and post-EBOV (B) Challenge. Plaque assays were done on serum collected from guinea pigs 7 days post-challenge. The data show that no viremia was detected in animals vaccinated with chimeras containing a GP1 subunit homologous to challenge virus (M/M or M/E challenged with MBGV, E/E or E/M challenged with EBOV). Virus was detectable in the serum of animals vaccinated with chimeras containing the homologous GP2 subunit (E/M for MBGV, M/E for EBOV), although at much reduced levels compared to animals vaccinated with heterologous VRP-GP (E/E for MBGV, M/M for EBOV). Numbers above each bar indicate viremic/total; where there were multiple viremic animals a GMT was calculated.

FIG. 8. ELISA with detergent-disrupted antigen to detect anti-GP2-reactive antibodies. Reactivity of (A) E/M vaccinated animals with MBG antigen or (B) M/E vaccinated animals with EBO antigen. Antigen was either native (N) or detergent-disrupted (DD; boiled in SDS+2ME) irradiated, sucrose purified virus. The data show that E/M prechallenge vaccinated animals had MBGV-GP2-reactive antibodies detectable only with detergent-disrupted virus, suggesting anti-GP2-specific antibodies which boosted in titer slightly after EBOV challenge. EBO-reactive antibodies were detected at a lower level in M/E vaccinated, pre-EBOV challenge animals. EBO-reactive antibodies were not detected in M/E vaccinated, pre-MBG challenge animals for unknown reasons, however these antibodies were detected (1.7 $\log_{10}$) when Triton X-100 was used to disrupt EBO antigen (data not shown).

FIG. 9. Western blot analysis to detect anti-MBGV-GP2-reactive antibodies. Sucrose purified, irradiated MBGV was electrophoresed under reducing conditions by 4-15% gradient SDS-PAGE. The protein was transferred to nitrocellulose and the blot divided and probed with convalescent guinea pig sera from MBGV or EBOV infected guinea pigs (α-MBGV sera and α-EBOV sera), or sera from pre-challenge animals vaccinated with VRPs expressing M/E (α-M/E) or E/M (α-E/M sera) chimeras. For reference, Biotinylated molecular weight markers were run with each of the four samples. The proteins were detected with Biotinylated goat-anti-guinea pig secondary antibody and avidin-conjugated Cy3. MBGV-GP2-specific antibodies were clearly present in the sera from E/M vaccinated animals (lane 1).

DETAILED DESCRIPTION

Figure 1:
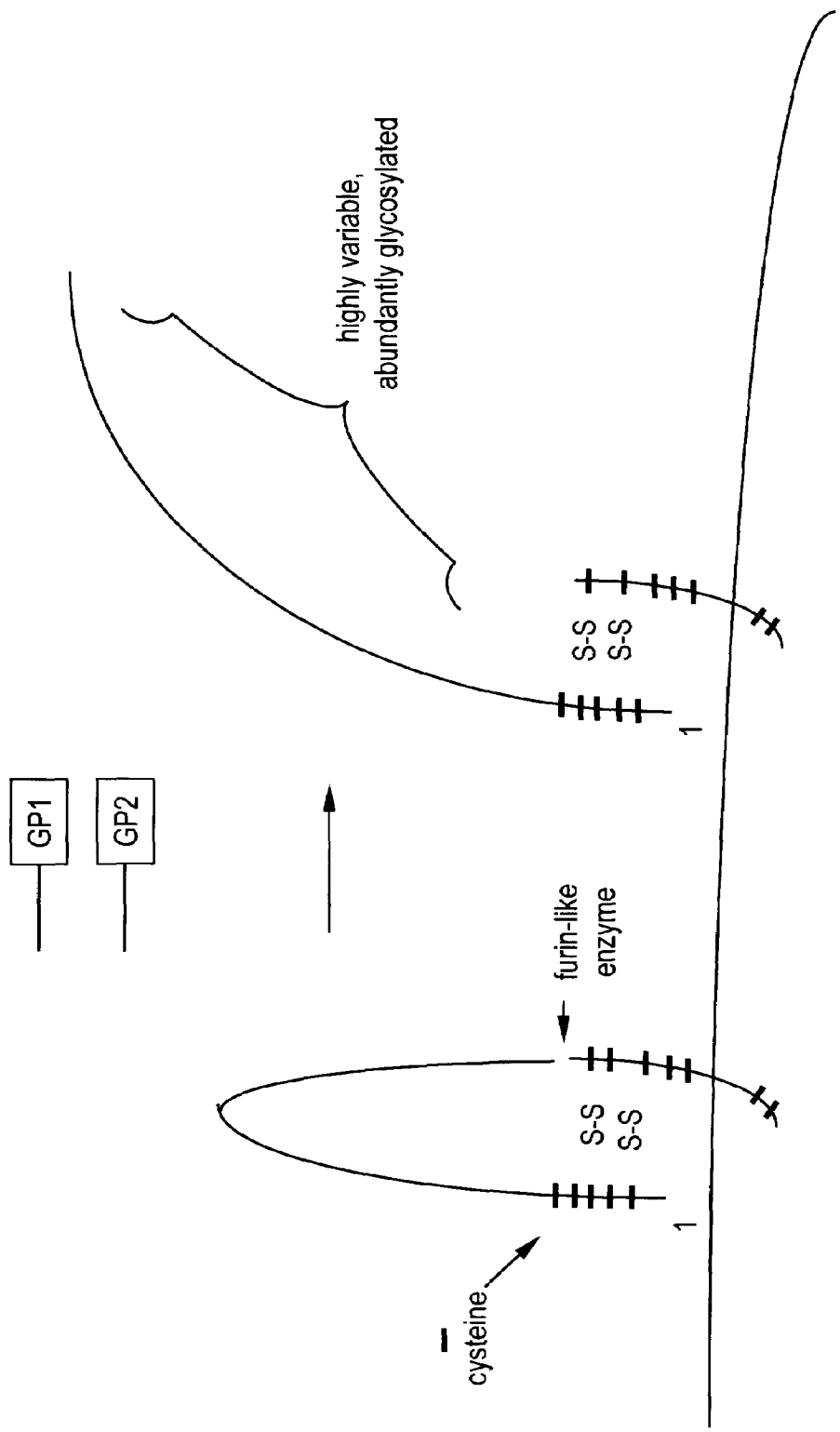
FIG. 1 is a schematic of filovirus GP proteins. GP is a highly glycosylated type 1 transmembrane protein. Following cleavage by a furin-like protease, mature GP consists of two disulfide-linked subunits, GP1 and GP2, which are anchored to the virion membrane by the transmembrane domain found within the GP2 subunit. The carboxyl-terminus of GP1 is highly variable among filoviruses.

In the description that follows, a number of terms used in recombinant DNA, virology and immunology are extensively utilized. In order to provide a clearer and consistent understanding of the specification and claims, including the scope to be given such terms, the following definitions are provided.

Filoviruses. The filoviruses (e.g. Marburg virus, MBGV) cause acute hemorrhagic fever characterized by high mortality. Humans can contract filoviruses by infection in endemic regions, by contact with imported primates, and by performing scientific research with the virus. However, there currently are no available vaccines or effective therapeutic treatments for filovirus infection. The virions of filoviruses contain seven proteins which include a surface glycoprotein (GP), a nucleoprotein (NP), an RNA-dependent RNA polymerase (L), and four virion structural proteins (VP24, VP30, VP35, and VP40). Little is known about the biological functions of these proteins and it is not known which antigens significantly contribute to protection and should therefore be used to induce an immune response by an eventual vaccine candidate. No antigenic cross-reactivity between the Genus Marburg virus and Ebola virus (the only two Genera in the Order Filoviridae). Marburg has species Musoke, Ravn, Popp, and strains Ozolin, Ratayczak, Voege (Musoke and Ravn are the most divergent of the Marburg viruses). Ebola has species Zaire (Strain Mayinga, Strain Zaire, Strain Eckron, Strain Tandala, Strain Kikwit, Strain Gabon), Sudan (Strain Boniface, Strain Maleo), Reston (Strain Reston, Strain Philippines, Strain Siena, Strain Texas), and Cote d'Ivoire (Strain Cote d'Ivoire). All filoviruses have GP proteins that have similar structure and cleave into GP1 and GP2 subunits. Amino acid homologies of surface glycoproteins of different representatives of the family Filoviridae, made from alignments of different Ebola viruses and one Marburg virus strains are known and can be found in Netesov et al., "Family Filoviridae", In *Virus Taxonomy*, Seventh Report of the International Committee on Taxonomy of Viruses, Ed. M. H. V. van Regenmortel et al., Academic Press, pp. 539-548.

Replicon. A replicon is equivalent to a full length virus from which all of the viral structural proteins have been deleted. A multiple cloning site can be cloned into the site previously occupied by the structural protein genes. Virtually any heterologous gene may be cloned into this cloning site. Transcription of the RNA from the replicon yields an RNA capable of initiating infection of the cell identical to that seen with the full-length infectious virus clone. However, in lieu of the viral structural proteins, the heterologous antigen is expressed. This system does not yield any progeny virus particles because there are no viral structural proteins available to package the RNA into particles.

Particles which appear structurally identical to virus particles can be produced by supplying structural proteins for packaging of the replicon RNA in trans. This is typically done with two helpers also called defective helper RNAs. One helper consists of a full length infectious clone from which the nonstructural protein genes and the glycoprotein genes are deleted. The helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then by inoculated into animals similar to parent virus. The replicon particles will initiate only a single round of replication because the helpers are absent, they produce no progeny virus particles, and express only the viral nonstructural proteins and the product of the heterologous gene cloned in place to the structural proteins.

The VEE virus replicon is a genetically reorganized version of the VEE virus genome in which the structural proteins genes are replaced with a gene from an immunogen of interest, in this invention, the MBGV virion proteins. The result is a self replicating RNA (replicon) that can be packaged into infectious particles using defective helper RNAs that encode the glycoprotein and capsid proteins of the VEE virus.

Subject. Includes both human, animal, e.g., horse, donkey, pig, guinea pig, mouse, hamster, monkey, chicken, bats, birds and insects such as mosquito.

In one embodiment, the present invention relates to a recombinant DNA molecule that includes a DNA sequence encoding a chimeric protein comprising different regions of filovirus glycoprotein, GP, from different filoviruses. In this application, chimeric proteins were produced using GP from Marburg Musoke (MBGV) and Ebola Zaire Mayanga strain (EBOV) as an example of chimeric proteins from different genera of filoviruses and from the most divergent of all the filoviruses. In addition, chimeric proteins from the most divergent of the Marburg viruses, Musoke (MUS) and Ravn (RVN) were produced as an example of chimeric proteins within the same genus. Accordingly, other species and strains of filovirus can be used to construct a chimeric GP protein since the homology between the filoviruses is known. Percent homologies between the glycoprotein (GP) protein sequences of 5 strains of Marburg virus and Ebola Zaire (Mayinga) are shown below and obtained from Sanchez, A., Trappier, S. G., Stroher, U., Nichol, S. T., Bowen, M. D., and Feldmann, H. (1998). Variation in the glycoprotein and VP35 genes of Marburg virus strains. *Virology* 240:138-146. It is expected that additional filovirus isolates or strains not listed and not yet discovered can be manipulated as described above and below in order to obtain an chimeric GP protein.

|  | POP | RYC | MUS | OZO | RAV | EBO-Zaire (Mayinga) |
|---|---|---|---|---|---|---|
| POP |  |  |  |  |  |  |
| RYC | 100 |  |  |  |  |  |
| MUS | 93.5 | 93.5 |  |  |  |  |
| OZO | 91 | 91.0 | 91.0 |  |  |  |
| RAV | 77.7 | 77.7 | 78.1 | 77.0 |  |  |
| EBO-Zaire (Mayinga) | 30.6 | 30.6 | 31.1 | 31.0 | 30.5 |  |

The complete nucleotide sequence for GP from each of these filoviruses is known: Marburg-Musoke, Feldmann et al., 1992, Virus Res. 24, 1-19 (Genbank accession #Z12132 S55429), Marburg-Ravn, Sanchez et al., 1998, Virology 240, 138-146 (Genbank accession #AF005734), Ebola Zaire Mayinga strain, Sanchez et al., 1993, Virus Res. 29, 215-240 (Genbank accession #U23187).

More specifically, chimeric proteins described in the examples below are presented in Table 1.

TABLE 1

| Chimeric proteins | | |
|---|---|---|
|  | SEQ ID NO: | |
| Chimera | nucleotide | Amino Acid |
| EBOV-GP1/MBGV-GP2 (E/M) | 1 | 2 |
| MBGV-GP1/EBOV-GP2 (M/E) | 3 | 4 |
| MUS-GP1/RVN-GP2 (M/R) | 5 | 6 |
| RVN-GP1/MUS-GP2 (R/M) | 7 | 8 |
| MBGV-GP1/GP2 (M/M control) | 9 | 10 |
| EBOV-GP1/GP2 (E/E control) | 11 | 12 |
| RVN-GP1/GP2 (R/R control) | 13 | 14 |

All chimeras contain a restriction site created in the chimeric proteins. The restriction site was introduced in the three nucleotides flanking either side of the furin cleavage site. The nucleotide changes introduced to engineer the Pvu1 restriction enzyme site are silent in the MBGV GP protein, and change the first amino acid of EBOV-GP2 from glutamic acid to serine (serine is the first amino acid of MBGV GP2).

It is understood that any portion of the a filovirus, e.g. EBOV, GP protein can be fused to any portion of another filovirus's, e.g. MBGV, GP protein as long as the chimeric protein produced induces an effective immune response. Other chimeras from two or more filoviruses could be produced by, for example, swapping portions (say, in 25, 50, 100aa "chunks") of the GP variable region (variable region defined between amino acids ~300-500 of all filovirus GP proteins), or adding the full variable region of one GP to the full sequence from the GP of a second strain of filovirus (tandem variable regions, increasing the overall length of the GP).

For more than two filoviruses, chimeras can be designed to include different amino acid segments from the variable region of multiple filovirus GPs, so the resulting chimeric protein would be expected to protect against all strains represented in the chimeric GP molecule. For example, if a protective epitope can be defined within a 50aa region of protein, then four protective epitopes (ie 50aa chunks) can be combined within the variable region of a single GP to protect against four different filovirus strains and this would apply for either or both GP1 and GP2, e.g. chimeric GP containing the GP2 subunit derived from different filovirus strains, with either a wild type (wt) or chimeric GP1 subunit derived from yet a third filovirus strain (wt) or a combination of multiple additional filovirus strains (chimera). Any combination of multiple regions of undetermined size along the length of the entire GP protein (including both GP1 and GP2), derived from any combination of any filovirus strains.

The chimeric protein, i.e. the protective antigen, can be cloned into different vaccine vectors for delivery to a subject.

When the DNA sequences described above are in an expression system, such as the VEE replicon described above, the proteins can be expressed in vivo. The DNA sequence for any of the MBGV or EBOV virion proteins described above can be cloned into the multiple cloning site of a replicon such that transcription of the RNA from the replicon yields an infectious RNA containing the sequence(s) which encodes the MBGV/EBOV chimeric virion protein or proteins of interest. Use of helper RNA containing sequences necessary for encapsulation of the viral transcript will result in the production of viral particles containing replicon RNA which are able to infect a host and initiate a single round of replication resulting in the expression of the MBGV/EBOV chimeric virion proteins. The sequences encoding the MBGV proteins and the EBOV proteins were cloned into the replicon vector by methods known in the art and described below in Materials and Methods. The VEE constructs (described in Table 2) containing Marburg and Ebola chimeric proteins can be used as a DNA vaccine, or for the production of RNA molecules as described below.

TABLE 2

Chimeric EBOV/MBGV GP VEE constructs

| GP1/GP2 | Construct |
|---|---|
| E/E | EBOV-MAY GP1 (aa1–501)/EBOV-MAY GP2 (aa502–676) |
| M/M | MBGV-MUS GP1 (aa1–435)/MBGV-MUS GP2 (aa436–681) |
| M/E: | MBGV-MUS GP1 (aa1–435)/EBOV-MAY GP2 (aa502–676) |
| E/M: | EBOV-MAY GP1 (aa1–501 )/MBGV-MUS GP2 (aa436–681) |
| Rvn/Mus: | MBGV-RVN GP1 (aa1–435)/MBGV-MUS GP2 (aa436–681) |

TABLE 2-continued

Chimeric EBOV/MBGV GP VEE constructs

| GP1/GP2 | Construct |
|---|---|
| Mus/Rvn: | MBGV-MUS GP1 (aa1–435)/MBGV-RVN GP2 (aa436–681) |
| Rvn/Rvn: | MBGV-RVN GP1 (aa1–435)/MBGV-RVN GP2 (aa436–681) |

Abbreviations:
MGBV = Marburg
EBOV = Ebola
MUS = Marburg strain Musoke
RVN = Marburg strain Ravn
MAY = Ebola strain Zaire-Mayinga
GP1 = GP1 subunit of GP protein
GP2 = GP2 subunit of GP protein
aa = amino acid (in these instances referring to the amino acid number/position in the wild-type sequence)

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see Current *Protocols in Molecular Biology*. Frederick M. Ausubel et al. (eds.), John Wiley and Sons, Inc. The RNA molecules can be used, for example, as a direct RNA vaccine, or to transfect cells along with RNA from helper plasmids, one of which expresses VEE glycoproteins and the other VEE capsid proteins, as described above, in order to obtain replicon particles.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Please see e.g., Maniatis, Fitsch and Sambrook, *Molecular Cloning; A Laboratory* Manual (1982) or *DNA Cloning*, Volumes I and II (D. N. Glover ed. 1985) for general cloning methods. The DNA sequence can be present in the vector operably linked to a sequence encoding an IgG molecule, an adjuvant, a carrier, or an agent for aid in purification of MBGV or EBOV virion proteins, such as glutathione S-transferase. The recombinant molecule can be suitable for transfecting eukaryotic cells, for example, mammalian cells and yeast cells in culture systems. *Saccharomyces cerevisiae, Saccharomyces carlsbergensis*, and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as CHO cells, vero cells, and COS cells to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art.

The transformed or transfected host cells can be used as a source of DNA sequences described above. When the recombinant molecule takes the form of an expression system, the transformed or transfected cells can be used as a source of the protein cloned into the VEE replicon, or a source of RNA transcribed from the replicon as described above, or a source of replicon particles.

In a further embodiment, the present invention relates to a method of producing the recombinant or chimeric protein which includes culturing the above-described host cells, under conditions such that the DNA fragment is expressed and the recombinant or fusion protein is produced thereby. The recombinant or chimeric protein can then be isolated using methodology well known in the art. The recombinant or chimeric protein can be used as a vaccine for immunity against infection with MBGV or EBOV or as a diagnostic tool for detection of MBGV or EBOV infection. The transformed host cells can be used to analyze the effectiveness of drugs and agents which inhibit MBGV or EBOV virus function, such as host proteins or chemically derived agents or other proteins which may interact with the virus to inhibit its replication or survival.

In another embodiment, the present invention relates to a single-component vaccine protective against several filoviruses. In a specific embodiment the filoviruses are MBGV and EBOV. It is understood, that protection against infection with other filoviruses can be achieved by using the concept of the present invention described for MBGV and EBOV since all filoviruses have GP proteins that have similar structure and cleave into GP1 and GP2 subunits. Other filoviruses include Genus Marburg virus and Ebola virus (the only two Genera in the Order Filoviridae). Marburg has species Musoke, Ravn, Ozolin, Popp, Ratayczak, Voege. Ebola has Strain Zaire, Sudan, Reston, and Cote d'Ivoire (with 1-6 species under each strain). A specific vaccine of the present invention comprises one or more replicon particles derived from one or more replicons encoding one or more MBGV and EBOV glycoproteins.

The present invention also relates to a method for providing immunity against MBGV and EBOV virus said method comprising administering one or more replicon particles containing any combination of the MBGV and EBOV glycoproteins to a subject such that a protective immune reaction is generated. Even though the MBGV strain Musoke was used in the examples below, it is expected that protection would be afforded using virion proteins from other MBGV strains and isolates, and/or other EBOV strains and isolates.

Vaccine formulations of the present invention comprise an immunogenic amount of a replicon particle, resulting from one of the replicon constructs described above, or a combination of replicon particles as a multivalent vaccine, in combination with a pharmaceutically acceptable carrier. An "immunogenic amount" is an amount of the replicon particles sufficient to evoke an immune response in the subject to which the vaccine is administered. An amount of from about $10^5$ to $10^8$ or more replicon particles per dose with one to three doses one month apart is suitable, depending upon the age and species of the subject being treated. Exemplary pharmaceutically acceptable carriers include, but are not limited to, sterile pyrogen-free water and sterile pyrogen-free physiological saline solution.

Administration of the replicon particles disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more constructs or replicating RNA described above can be use in any combination effective to illicit an immunogenic response in a subject. Generally, the nucleic acid vaccine administered may be in an amount of about 1-5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following MATERIALS AND METHODS were used in the examples that follow.

Cells and viruses. BHK, Vero, and Vero E6 cells were maintained in minimal essential medium with Earle's salts (EMEM) supplemented with 10% heat inactivated fetal bovine serum (FBS) and 2% penicillin (20,0001 IU/ml)/streptomycin (20 mg/ml). MBGV strain Musoke was isolated from a human case of infection in Kenya in 1980 (Smith et. al., 1982, Lancet 1, 816-820). This virus was adapted to guinea pig lethality by eight passages in strain-13 guinea pigs followed by three passages and plaque purification on Vero E6 cells (Hevey et. al., 1997, Virology 251, 28-37). EBOV strain Zaire strain Mayinga was passed six times in VeroE6, cells, twice on Vero cells, and an additional time on Vero E6 (Jharling et al., 1996, Arch. Virol. Suppl. 11, 135-147). MBGV and EBOV were grown in Vero E6 cells cultured to confluency in roller bottles. Cells were infected with MBGV or EBOV at a low moi (<0.05) and virus allowed to grow for 7 days, with EMEM+10% FBS replaced at 4 days post infection. Cell supernatant was harvested and clarified by centrifugation for 15 min at 1500 g, and virus yield was determined by plaque assay. To concentrate virus for use as ELISA antigen, virus was pelleted by additional centrifugation of the culture supernatant at 10,000 g for 30 min. Pelleted virus was resuspended in TNE (10 MM Tris pH 7.4, 150 mM NaCl, 1 mM EDTA), layered over 20-60% sucrose-TNE gradient, and centrifuged at 38,000 rpm (SW41 rotor) for 4 hr. The visible virus band was collected, aliquoted, and irradiated (6 MR, $^{60}$Co source). Virus was safety tested for the absence of infectivity in tissue culture.

Cloning of chimeric GP genes. Chimeric GP proteins were constructed by swapping the GP1 and GP2 subunits between EBOV strain Zaire Mayinga strain and MBGV strain Musoke. The GP1 and GP2 portions were cloned by PCR and joined by introduction of a unique Pvu1 restriction site created in the three nucleotides flanking either side of the furin cleavage site. The nucleotide changes introduced to engineer the Pvu1 restriction enzyme site are silent in the MBGV GP protein, and change the first amino acid of EBOV-GP2 from Glu to Ser (Ser is the first aa of MBGV GP2). The GP1 forward and GP2 reverse primers were tailed with HindIII and EcoRI restriction enzyme sites, respectively, and following ligation of the GP1 and GP2 PCR products at the Pvu1 restriction site, the full-length GP genes were ligated into the VEE shuttle vector using HindIII and EcoRI. The chimeric and wt GPs were then excised from shuttle vector and ligated into the VEE replicon plasmid using ClaI, and screened for orientation before expression. The VEE constructs are described in Table 2.

The primers used for cloning were as follows: GP1 forward (containing HindIII) EBOV (5'-CAA GCT TCA ATG GGC GTT ACA-3', SEQ ID NO:15), MBGV (5'-AAG CTT AAC ATG AAG ACC ACA T-3', SEQ ID NO:16); GP2 forward (containing Pvu1) EBOV (5'-GAC GAT CGG CAA TTG TCA ATG-3', SEQ ID NO:17), MBGV (5'-AGC GAT CGA TCC TCT GGA G-3', SEQ ID NO:18); GP1 reverse (containing PvuI) EBOV (5'-GCC GAT CGT CGA GTT CTT CT-3', SEQ ID NO:19), MBGV (5'-GAT CGA TCG CTT TCT TCT G-3', SEQ ID NO:20); GP2 reverse (containing EcoRI) EBOV (5'-TGA ATT CAA CTA AAA GAC AAA TTT G-3', SEQ ID NO:21), MBGV (5'-CGA ATT CCG TTA TCC GAT ATA T-3', SEQ ID NO:22). The original EBOV GP gene was provided by Dr. Tony Sanchez, CDC, Atlanta, Ga.; MBGV GP gene was provided by Drs. A. Sanchez and H. Feldmann.

The primers used for cloning the following three chimeras MBGV MUS-GP1 with MBGV RVN-GP2 (M/R), and MBGV-RVN-GP1 with MBGV MUS-GP2 (R/M) and MBGV RVN-GP1 with MBGV RVN-GP2 (R/R) were as follows: GP1 forward (containing HindIII) MBGV MUS (5'-AAG CTT AAC ATG AAG ACC ACA T-3', SEQ ID NO:23) MBGV RVN (5-AAG CTT CGA CAT GAA GAC CAT AT-3', SEQ ID NO:24); GP2 forward (containing Pvu1) MBGV MUS (5'-AGC GAT CGA TCC TCT GGA G-3', SEQ ID NO:25), MBGV RVN (5'-AAC GAT CGA TTT TCT GGA A-3', SEQ ID NO:26); GP1 reverse (containing PvuI) MBGV MUS (5'-GAT CGA TCG CTT TCT TCT G-3', SEQ ID NO:27), MBGV RVN (5'-AAA TCG ATC GTT TCT TTC TAA AG-3', SEQ ID NO:28); GP2 reverse (containing EcoRI) MBGV MUS (5'-CGA ATT CCG TTA TCC GAT ATA T-3', SEQ ID NO:29), MBGV RVN (5'-CGA ATT CTG TCA TCC AAT GTA T-3', SEQ ID NO:30). M/R, R/M, and R/R were cloned into shuttle vector with HindIII EcoRI, then moved to replicon vector with ClaI.

VEE replicons: Production and Quantification. Viral replicon particles (VRPs) were packaged as described previously (Pushko et al., 1997, Virology 239, 389-401). Briefly, replicon RNA was transcribed in vitro which contains the VEE non-structural protein genes and the wt or chimeric GP gene. The replicon RNA was cotransfected, along with two in vitro transcribed helper RNAs coding for the VEE glycoproteins and the VEE capsid protein, to provide the structural proteins in trans, into BHK cells. The replicon RNA contains the authentic VEE packaging signal (which the helper RNAs lack) and is therefore incorporated into VRPs. Infectious, replication-incompetent replicons were collected from the culture supernatant 24 and 40 hrs after transfection, and concentrated by pelleting through a 20% sucrose-TNE cushion (10 mM Tris pH 7.2, 150 mM NaCl, 1 mM EDTA) for 4 hr at 25,000 rpm (SW28 rotor), and resuspended in 1 ml PBS. Packaged replicons were titered by serial dilution on Vero cells cultured in chamber slides (LabTek, Nunc, Inc., $1 \times 10^5$ cells/well). VRPs were allowed to infect the Vero cells for 18 h at 37° C. to allow the wt and chimeric GPs to be expressed. The cells were then fixed for 20 min in acetone, and antigen-positive cells detected by indirect immunofluorescence (IFA) as described previously (Schmaljohn et al., 1995, Virology 206, 963-972) using polyclonal guinea pig anti-EBOV and guinea pig anti-MBGV. The negative control replicon expressing Lassa NP protein was quantitated similarly, as described previously (Hevey et al., 1998, Vaccine 20, 586-593).

Immunoprecipitation. VRP-expressed proteins were assayed by immunoprecipitation using polyclonal guinea pig anti-EBOV (kindly provided by Joan Geisbert, USAMRIID, and from E/E vaccinated, EBOV challenged convalescent animals presented here) or guinea pig anti-MBGV (from M/M vaccinated, MBGV challenged convalescent animals presented here and Hevey et al., 1997, supra). To generate radiolabeled wt or chimeric GP protein, Vero cells were infected with VRP at moi=3 in 6-well plates and incubated at 37° C. for 18 hr. Complete medium was removed, cells were starved for 30 min in 1× MEM cystine/methionine free media (ICN, Inc., Aurora, Ohio), and then labeled for 4 hr in cys/met-free media supplemented with 50 uCi/ml $S^{35}$-cystine, 50 uCi/ml $S^{35}$-methionine, and 2% FBS. Supernatant was collected, cells were washed once with Zwittergent wash buffer (0.4% Zwittergent, 0.5M NaCl, 10 mM Tris pH 8.0, 1 mM EDTA) and lysed by incubation in 500 ul Zwittergent lysis buffer (4% Zwittergent, 0.5M NaCl, 10 mM Tris pH 8.0, 1 mM EDTA) for 5 min on ice with rocking. To prepare antibody, polyclonal sera was adsorbed to magnetic Protein A beads (Dynal, Oslo, Norway) in a ratio of 15 ul antibody:50 ul bead slurry per sample, for a minimum of 1 h at 4° C. with continuous rocking. Unbound antibody was washed from beads with 0.5 ml Zwittergent wash buffer using a magnetic particle concentrator (MPC; Dynal) for separation of magnetic beads form supernatant. Beads were resuspended to a volume of 50 ul/sample in Zwittergent lysis buffer (0.4% Zwittergent, 0.5M NaCl, 10 mM Tris pH 8.0, 1 mM EDTA) and 50 ul beads then added to 50 ul cell extract or cell supernatant. Antigen was allowed to bind the antibody-coated magnetic beads for 4 h at 4° C. with continuous rocking. Beads were washed three times in Zwittergent wash buffer and then resuspended in 30 ul 2× Laemmli sample buffer (BioRad, Hercules, Calif.)+5% 2-mercaptoethanol. Samples were then incubated for 5 min at 95° C., the beads magnetically separated, and 15 ul supernatant was electrophoresed on a 5-15% gradient SDS-PAGE.

Guinea Pig Vaccination. To test protective efficacy, five groups of inbred strain 13 guinea pigs, consisting of 12 animals per group, received 2 doses of $10^6$ focus forming units (ffu) of replicon expressing M/M, M/E, E/E, or E/M 28 days apart (a schedule that has been previously demonstrated to be protective; Hevey et al., 1998) (FIG. 5). Animals were vaccinated subcutaneously with 0.5 ml total volume administered at two dorsal sites. As a control, animals were immunized with Lassa NP, an irrelevant VRP-expressed antigen. Animals were anesthetized and bled at the time of each vaccination (days 0 and 28) and before challenge (~day 50) in order to measure antibody responses of vaccinated animals by ELISA. Half the immunized animals in each group were challenged with a guinea pig adapted Marburg virus (strain Musoke) and the other half with a guinea pig adapted Ebola virus (strain Zaire-Mayinga) 23-28 days after the second vaccine administration. Heparinized plasma was collected from the retroorbital sinus of anesthetized animals on days 7 and 14 post-challenge in order to measure serum viremia. Surviving animals were monitored for 30-45 days post-challenge, anesthetized, and exsanguinated to obtain convalescent serum.

ELISA. Antibody titers against EBOV and MBGV GP were determined pre-and post-challenge by indirect ELISA. Antigen consisting of sucrose-purified, irradiated MBGV or EBOV was used to coat PVC 96-well microtiter ELISA plates (Dynex Technologies Laboratories, Chantilly, Va.) at a dilution empirically determined to result in optimal reactivity, usually 1:1000-1:2000, 50 ul/well in PBS incubated overnight at 4° C. Nonspecific binding was blocked by incubation with 200 ul/well PBS+0.02% Tween-20 (PBST) with 5% nonfat dry milk, for 1 hr at room temperature. Plates were then washed five times with 200 ul/well PBST. Serum was tested by making half-log dilutions (3.16-fold) in PBST+5% milk and 1% FBS, 50 ul/well, aliquoted in duplicate down the plate, generating eight concentrations for each sample. Primary antibody was incubated with the antigen for 1 hr at room temperature, followed by washing five times in PBST. Secondary antibody was 100 ul/well of horseradish peroxidase (HPO)-conjugated goat anti-guinea pig IgG(H+L) (Kirkegaard and Perry laboratories, Gaithersburg, Md.), used at a 1:2000 dilution in PBST+5% milk and 1% FBS, incubated for 1 hr at room temperature, followed by washing five times in PBST. Colormetric peroxidase substrate, 2,2'-azinobis-[3-ethylbenzothizoline-6-sulfonic acid] diammonium salt (ABTS; Kirkegaard and Perry laboratories, Gaithersburg, Md.), was added, 100 ul/well. After 30 min at room temperature the optical density at 405 nm of each well was determined using SpectroMAX340 (Molecular devices, Sunnyvale, Calif.). Endpoints were calculated for each dilution series using SOFTmaxPro software (Molecular devices Corp.), using a curve-fit of background-subtracted mean OD versus dilution, and subsequent extrapolation of the dilution at which OD=0.2. Results are shown in FIGS. 4-6 are from a single assay each to allow valid comparisons between groups.

Plaque Assay. Plaque assays were performed as described previously (Moe et al., 1981, J. Clin. Microbiol. 13, 791-793). Briefly, ten-fold serial dilution of samples to be tested were made on Vero E6 cells cultured in 6-well plates. One hundred microliters of each virus dilution was adsorbed to monolayers for 1 hr at 37° C., followed by a 0.5% agarose-1× EBME overlay. Six days post infection a second overlay of 20% Neutral Red solution in 0.5% agarose-1× EBME was added to visualize plaques. The neutral red overlay was incubated for an additional 24 hr at 37° C., and plaques were counted on day 7.

Western blot. Sucrose purified, irradiated EBOV or MBGV diluted 1:50 in PBS was heated for 5 min at 95° C. in 2× Laemmli sample buffer (BioRad, Hercules, Calif.)+5% 2-mercaptoethanol prior to separation by gel electrophoresis. Proteins were electroblotted onto Immobilon-P nitrocellulose (Millipore, Bedford, Mass.). After blocking in PBST+5% nonfat dry milk, the blots were washed and incubated with vaccinated, pre-challenge guinea pig sera in PBS+0.02% Tween-20 (PBST) for 1 hr with rocking. Secondary antibody was a 1:1000 dilution of biotinylated goat-anti-guinea pig IgG(H+L) (Kirkegaard and Perry laboratories, Gaithersburg, Md.), incubated for 1 hr in PBST with rocking. Protein was detected with a 1:1000 dilution of avidin-conjugated Cy3 (Kirkegaard and Perry laboratories, Gaithersburg, Md.), and visualized using the Typhoon 8600 Scanner (Molecular Dynamics, Amersham Pharmacia Biotech, Inc., Piscataway, N.J.).

Indirect immunofluorescence assay (IFA). Cultured Vero cells were infected with replicons expressing the wt or chimeric GP proteins, or the Lassa NP protein. One day post infection the cells were trypsinized, washed with PBS, dried on 10-well teflon-etched spot slides (Cell-Line Associates, Inc., Newfield, N.J.), and fixed in acetone for 20 min at −20° C. Antigen was detected by incubation with polyclonal guinea pig sera for 30 min at room temperature, diluted 1:50 in PBS+1%FBS for a total of 20 ul/spot. Slides were then washed for 30 min submerged in PBS with stirring. A secondary FITC-conjugated anti-guinea pig antibody (made in-house at USAMRIID) was used at a 1:40 dilution in PBS+1%FBS, 20 ul/well, incubated for 30 min at RT, and the slides washed again for 30 min in PBS. Fluorescing cells were imaged using Carl Zeiss Imaging system (AxioPlan light microscope, AxioCam CCD camera, and AxioVision 2.05 image capture software, 1999; Carl Zeiss, Inc., West Germany).

EXAMPLE 1

Chimeric GP VEE Replicon Constructs

Figure 2:
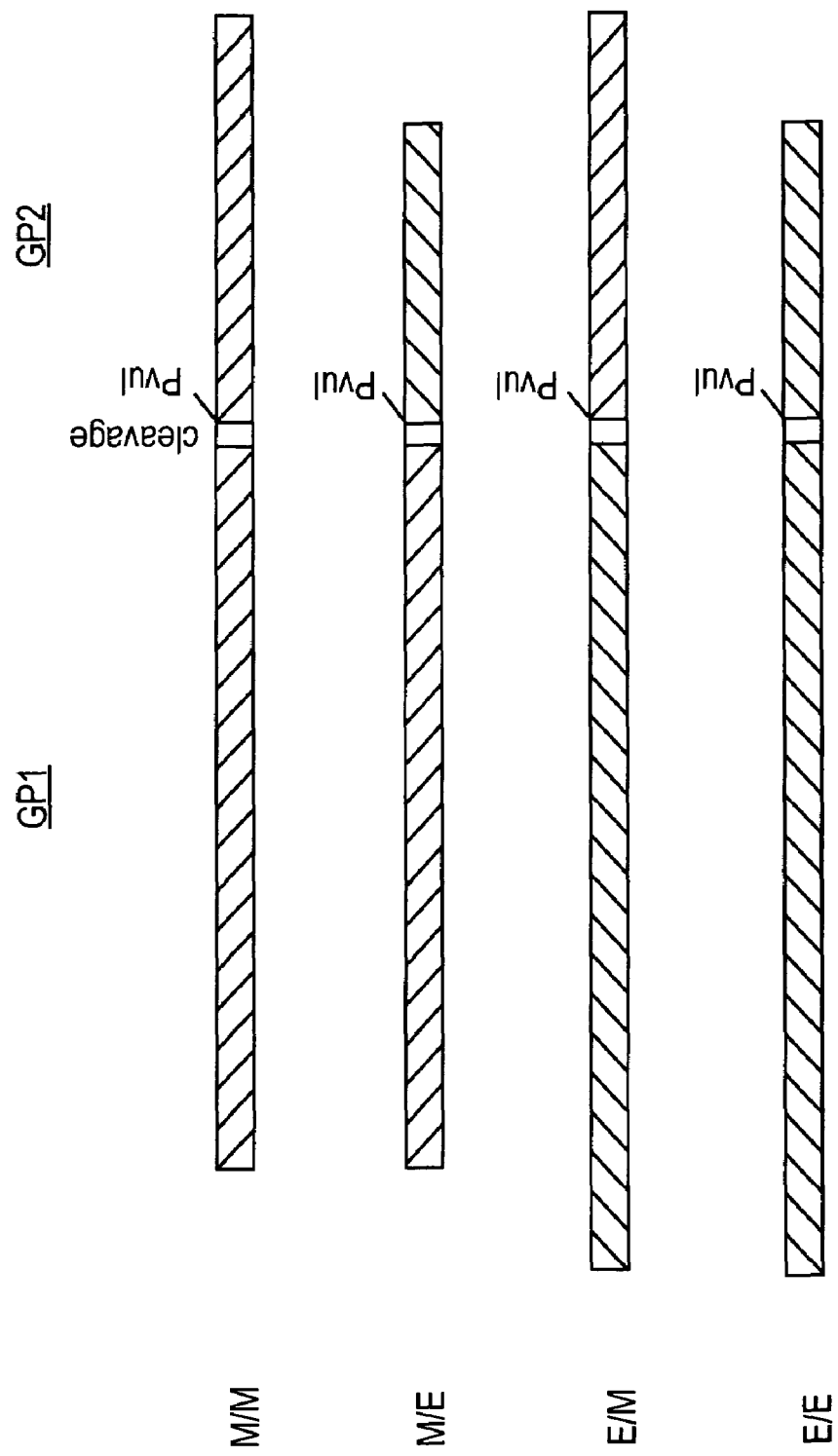
FIG. 2. MBGV/EBOV Chimeric GP genes. The chimeras were created by cloning the GP1 and GP2 portions by PCR and joined by an engineered unique silent Pvu1 restriction site immediately downstream of the furin cleavage site. MBGV strain Musoke GP protein is 681 aa (GP1, 436 aa; GP2 245 aa) and EBOV strain Zaire, strain Mayinga GP is 676 aa (PG1 501 aa; GP2 175 aa).

Filovirus GP proteins are post-translationally cleaved by a host cell furin-like protease into two disulfide-linked subunits, GP1 and GP2. Chimeric GP proteins were constructed by swapping the GP1 and GP2 subunits between EBOV strain Zaire (Mayinga) and MBGV strain Musoke. The furin cleavage site of each of these molecules was selected as the junction site as an attempt to minimize disruption of protein folding and tertiary structure and increase the likelihood of forming a stable molecule. Two chimeras were made: EBOV-GP1 with MBGV MUS-GP2 (E/M), and MBGV MUS-GP1 with EBOV-GP2 (M/E). As controls, the GP1 and GP2 portions of EBOV and MBGV were also cloned with the same Pvu1 restriction site, creating the equivalent of wild-type (wt) molecules EBOV-GP1 with EBOV-GP2 (E/E), and MBGV MUS-GP1 with MBGV MUS-GP2 (M/M) (FIG. 2).

Figure 3:
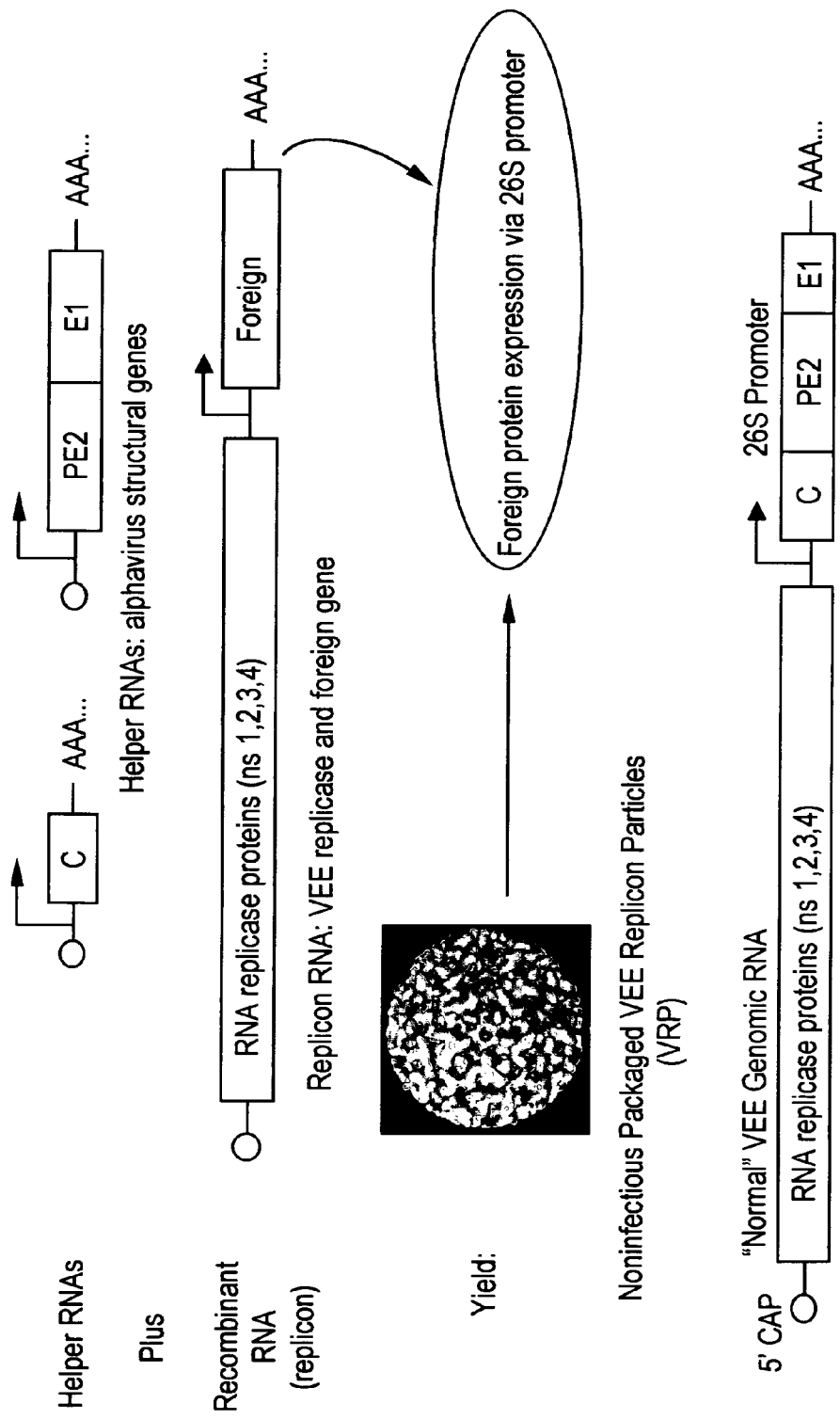
FIG. 3. The VEE replicon system. The VEE structural proteins are replaced with the immunogen of interest (in this case the chimeric GP genes) in a recombinant VEE RNA genome (the replicon), and when the VEE structural proteins are supplied in trans the replicon RNA is packaged into defective viral replicon particles (VRP). The packaged replicons are capable of infecting host cells and express large amounts of the foreign immunogen, but are incapable of spreading to new cells.

The chimeric molecules were cloned into the VEE replicon vector which offers the advantage of high protein expression levels in mammalian cells as well as serving as a proven vaccine vector (Hevey et al., 1998, supra; Pushko et al., 1997, supra). As depicted in FIG. 3, the VEE replicon vector system replaces the VEE structural proteins with the immunogen of interest (in this case the chimeric GP molecules) in a recombinant VEE RNA genome (the replicon RNA). The packaged viral replicon particles (VRPs) are capable of infecting host cells and express large amounts of the foreign immunogen, but are incapable of spreading to new cells.

Replicon-driven expression of the EBOV/MBGV wt and chimeric GP proteins was confirmed by immunoprecipitation using polyclonal guinea-pig anti-EBOV and guinea pig anti-MBGV sera (FIG. 4). Protein products of the expected sizes were specifically precipitated by the appropriate antisera, indicating antigenicity of the proteins was maintained. The apparent size of filovirus glycoproteins, approximately 170 kDa, is much larger than the predicted molecular weight because of the abundant glycosylation, and a heterogenous population of post-translationally modified GPs is typically observed by electrophoresis (Feldmann et al., 1991, Arch. Virol. 15, 159-169; Feldmann et al., 1994 Virology 199, 469-473; Volchkov et al., 1998, Proc. Natl. Acad. Sci. USA 95, 5762-5767; Will et al., 1993, J. Virol. 76, 1203-1210). EBOV GP1 (FIG. 4 lanes 5,6, and 11-12) and MBGV GP1 (FIG. 4 lanes 3-4, and 9-10) were detected in both the cell lysate and supernatant. EBOG GP2 was observed in lanes 3 and 4 at approximately 26 kDa, as expected (Volchkov 1998, supra), indicating the E/E and E/M chimeras were cleaved into GP1 and GP2 subunits. EBOV GP2 was present in the supernatant as well, although only in the context of E/E expressed protein (FIG. 4, lane 11). MBGV GP2, expected to be present at approximately 40-45 kDa (Volchkov et al., 2000, Virology 214, 421-30), was more difficult to detect is either the M/M or E/M construct. Lack of MBGV GP2 in the E/M construct was not thought to be a result of a problem with gene expression or disulfide bonding, because the MBGV GP2 was barely detectable in the M/M construct as well, and full-length GP protein was clearly produced in both instances (FIG. 4, lanes 3 and 6). The MBGV GP2 subunit could either be weakly radiolabeled, or uncleaved from the GP1 subunit under these particular protein expression conditions, thus running as the full-length GP even under reducing gel electrophoresis. A band corresponding to the expected size of sGP (Wilson et al., 2000, Science 287, 1664-1666) was present in the supernatant of cultures expressing E/E and E/M (FIG. 4, lanes 11-12). This was not wholly unexpected as the transcriptional editing site of EBOV GP is upstream of the furin cleavage site, such that both constructs with EBOV GP1 subunit could potentially be edited by the polymerase during transcription and therefore produce sGP. We have observed on multiple occasions that the VEE polymerase, in addition to the authentic viral polymerase and T7 polymerase (Volchkov et al., 1995, supra), is capable of editing the EBOV GP mRNA during transcription.

EXAMPLE 2

Protection of Guinea Pigs with GP Chimeras

Because cross protection between EBOV and MBGV GP has not been observed, the ability of the EBOV/MBGV chimeras to protect against either EBOV or MBGV infection was assessed in guinea pigs. To test protective efficacy, five groups, consisting of 12 guinea pigs each, received 2 doses of $10^6$ focus forming units of replicon expressing M/M, M/E, E/E, or E/M 28 days apart. As a control, animals were also immunized with Lassa NP, an irrelevant replicon-expressed antigen. Antibody responses of animals were monitored by ELISA before each inoculation and before challenge. Half the immunized animals in each group were challenged with ca. 1000LD$_{50}$ of guinea pig adapted MBGV (Musoke) and the other half with ca. 1000LD$_{50}$ EBOV (Zaire) 23-26 days after the second vaccine administration (FIG. 5).

Results from the guinea pig vaccination experiment are shown in Table 3. Animals vaccinated with M/E antigen were fully protected from MBGV challenge and almost completely (5 out of 6) protected from EBOV challenge. Similarly, E/M vaccinated animals were fully protected from either EBOV or MBGV challenge. The wt E/E protected animals from EBOV challenge while M/M did not; conversely M/M protein provided protection only against MBGV challenge, as would be expected based on lack of cross-protection between the two viruses observed in previous experiments. A single animal did survive MBGV infection after vaccination with E/E antigen, as did one animal vaccinated with the irrelevant Lassa NP protein as a negative control. These results indicate that vaccination with a chimera consisting of GP1 subunit homologous to challenge virus (E/M challenged with EBOV or M/E challenged with MBGV) fully protected animals from death. Additionally, and perhaps somewhat surprisingly, vaccination with chimeras having only the GP2 subunit homologous to virus challenge were completely (E/M challenged with MBGV) or nearly completely (M/E challenged with EBOV) protected from death.

TABLE 3

Protection of VRP-Chimeric GP Vaccinated Guinea Pigs from MBGV or EBOV Challenge

| Antigen | MBVG Challenge | | EBOV Challenge | |
|---|---|---|---|---|
| | S/T[a] | MDD[b] | S/T | MDD |
| M/M | 5/5 | — | 0/6 | 10 |
| M/E | 6/6 | — | 5/6 | 8 |
| E/E | 1/6 | 11 | 6/6 | — |
| E/M | 6/6 | — | 6/6 | — |
| LassaNP | 1/6 | 13 | 0/6 | 10 |

[a]S/T, survivors/total on day 30 post infection
[b]MDD, mean day of death

EXAMPLE 3

Antibody Responses to Vaccination and Lethal Virus Challenge

Figure 6A:
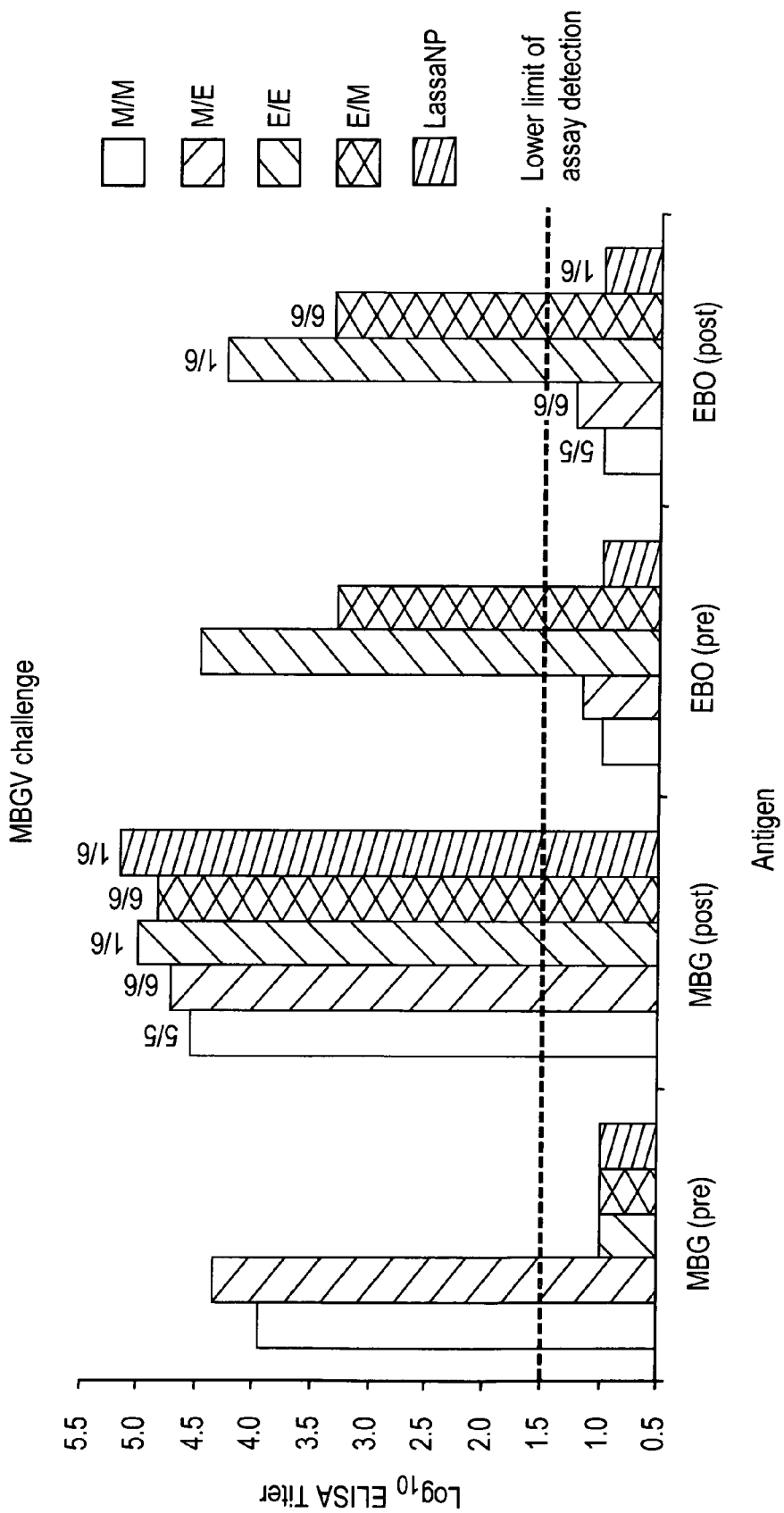
FIG. 6. Pre- and Post-MBGV and EBOV Challenge ELISA Titers. Sera from either pre- or post-MBGV (A) or EBOV (B) challenged guinea pigs was assayed for anti-Marburg (MBG) or anti-Ebola (EBO) antibodies using irradiated, sucrose-purified virus as antigen. Dashed line indicates lower limit of assay detection. Numbers above the bars indicate survivors/total; where there were multiple survivors a GMT was calculated. The data indicate that before challenge, anti-MBG titer was detected in the M/M, and M/E groups, while anti-EBO titer was detected in the E/E and E/M groups. Animals that had no detectable antibody titer pre-challenge showed a boost when challenged with homologous virus, indicating these animals were infected.
Figure 6B:
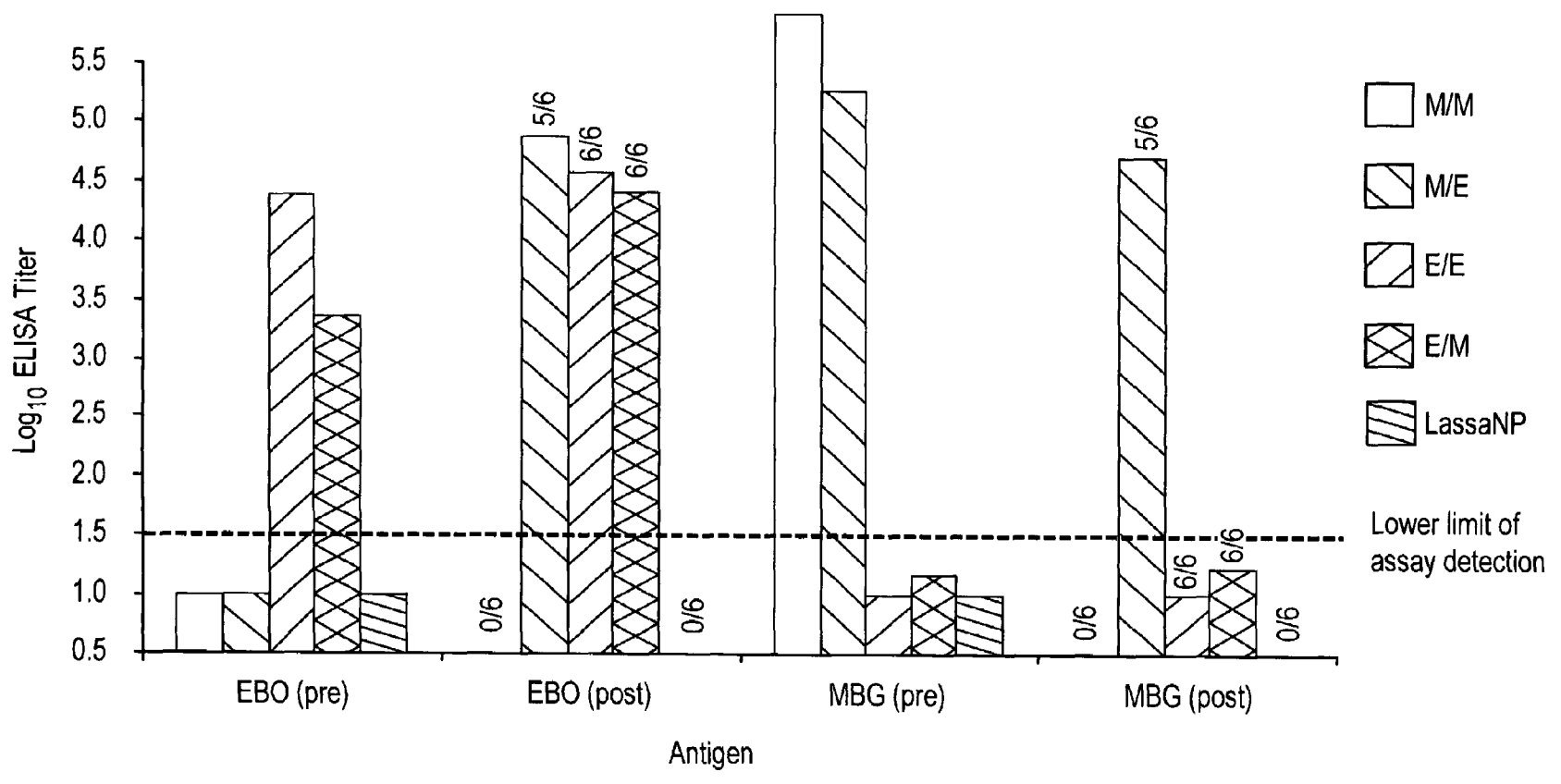

The pre- and post-challenge antibody titers of the guinea pigs vaccinated with the chimeras are presented in FIG. 6. The data indicate that before challenge, anti-MBGV specific antibodies were detected only in the M/M, and M/E groups, and not in the E/E, E/M, or Lassa NP control vaccinated animals [MBG(pre) antigen, FIGS. 6A and B]. Anti-EBOV reactive antibodies were detected in the E/E and E/M groups, but not in the M/M, M/E, or Lassa NP vaccinated animals [EBO(pre), FIGS. 6A and B]. Animals that had no detectable antibody titer to either MBGV or EBOV antigen pre-challenge showed a boost once challenged with the same virus, indicating these animals were indeed infected [MBG(post), FIG. 6A; EBO (post), FIG. 6B]. There was no increase in EBOV-reactive antibodies following MBGV challenge [EBO(pre) vs EBO (post) FIG. 6A], and conversely no boost in MBGV-reactive antibodies following EBOV challenge [MBG(pre) vs MBG (post) FIG. 6B], underscoring the lack of cross-reactivity between the two viruses.

EXAMPLE 4

Marburg and Ebola Virus Post-challenge Viremias

The post-challenge viremias are shown in FIG. 7. Seven days post-challenge, the Lassa-NP control animals had infectious virus in their sera, approximately 3.5 Log$_{10}$ PFU/ml in the EBOV challenged animals (FIG. 7A) and 5 Log$_{10}$ PFU/ml in the MBGV challenged animals (FIG. 7B). Back-titration of MBGV inoculum indicated that the challenge dose was lower than expected (350 pfu), which could explain the lower viremia in the MBGV-challenged LassaNP controls. Vaccination with wt GP protein derived from the challenge virus, M/M challenged with MBGV (FIG. 7A) and E/E challenged with EBOV (FIG. 7B), prevented viral replication and no infectious virus was detected in these animals at day 7. Detectable viremia was also absent in MBGV-challenged animals that had been vaccinated with M/E (FIG. 7A) and in EBOV-challenged animals vaccinated with E/M (FIG. 7B). Infectious virus was detectable in the serum of animals vaccinated with E/M and challenged with MBGV (FIG. 7A), and in animals vaccinated with M/E and challenged with EBOV (FIG. 7B). However the viremias present in those cases were at a much reduced level (~2-3 log decrease) compared to viremia found in the animals vaccinated with the corresponding wt GP (compare E/E with E/M vaccinated animals challenged with MBGV, FIG. 7A; M/M with M/E vaccinated animals challenged with EBOV, FIG. 7B). It is interesting to note that the LassaNP vaccinated MBGV survivor had no viremia on either day 7 or day 14. The E/E vaccinated MBGV survivor did have detectable viremia on day 7 (data not shown). One of the Lassa-NP vaccinated, MBGV challenged, animals had a delayed, but nonetheless lethal, disease course; this animal showed no viremia at day 7 but had detectable viremia (3.6 $Log_{10}$) at the time of death on day 14. No other animals were viremic on day 14 (data not shown). Thus, the data show that vaccination with a GP chimera containing the GP1 subunit homologous to the challenge virus prevented viral replication and induced "sterile" immunity (M/E challenged with MBGV, E/M challenged with EBOV). However, vaccination with a chimeric GP containing the homologous GP2 subunit (E/M for MBGV challenge, M/E for EBOV challenge), although preventing death in 11 out of 12 animals, did not completely prevent EBOV or MBGV replication after challenge with lethal virus dose.

EXAMPLE 5

Detection of Anti-GP2-reactive Antibodies

Because animals vaccinated with the much smaller GP2 subunit of GP were protected from lethal virus challenge, it was of interest to know whether these animals were mounting an antibody response to the GP2 subunit of their vaccine antigen. To begin exploring this idea, ELISAs were again performed using pre- and post-challenge sera of vaccinated animals and detergent-disrupted sucrose purified irradiated virus as antigen. Detergent disruption of antigen was carried out in 1% SDS+2-mercaptoethanol (2-ME), followed by 5 min at 95° C. before coating ELISA plates. The data show that before challenge, E/M vaccinated animals had MBGV-reacting antibodies detectable only with detergent-disrupted virus, and not with native virus, as antigen, suggesting the presence of anti-MBGV-GP2-specific antibodies (FIG. 8A, pre-MBGV and pre-EBOV). These antibodies boosted slightly in titer following EBOV challenge (FIG. 8A, post-EBOV). Ebola-GP2 reactive antibodies were detectable, although at a lower level, in M/E vaccinated, pre-EBOV challenge animals when detergent-disrupted EBOV was used as antigen. EBOV-GP2-reactive antibodies were not detected in M/E vaccinated, pre-MBGV challenge animals (compare native and detergent disrupted EBO antigen, FIG. 8B pre-MBGV). It is unknown why anti-EBOV-GP2 reactive antibodies would be detectable in only one of the two pre-challenge groups (FIG. 8B), however it is interesting to note that a titer for the M/E vaccinated, pre-MBGV group (1.7 $log_{10}$), similar to that seen in the M/E vaccinated pre-EBOV group, was observed when 1% Triton X-100 was used to disrupt the EBO antigen in place of SDS+2-ME (data not shown).

Western Blot analysis was also done in order to assay for the presence of GP2-specific antibodies. Sucrose purified, irradiated MBGV or EBOV antigen was separated by 4-15% SDS-PAGE, transferred to nitrocellulose, and detected with sera from vaccinated, pre-challenge animals. As shown in FIG. 9, MBGV GP1 and GP2 were detected in sera form animals vaccinated with M/M, as would be expected as a positive control, while no MBGV-reactive antibodies were detected in sera from E/E vaccinated animals (FIG. 9, lanes 4 and 2, respectively). M/E vaccinated animals had MBGV-GP1-reactive antibodies (FIG. 9, lane 3), as expected. Anti-MBGV-GP2-specific antibodies were clearly detected in the E/M vaccinated guinea pig sera (FIG. 9, lane 1). The search for EBOV-GP2 reactive antibodies by western blot analysis using EBOV separated by SDS-PAGE as antigen was inconclusive. EBOV GP1 was detected with E/E and E/M sera, however neither the E/E nor M/E sera detected the presence of EBOV GP2 (data not shown). Thus anti-MBGV-GP2 reactive antibodies were clearly detectable by western blot analysis.

Figure 10:
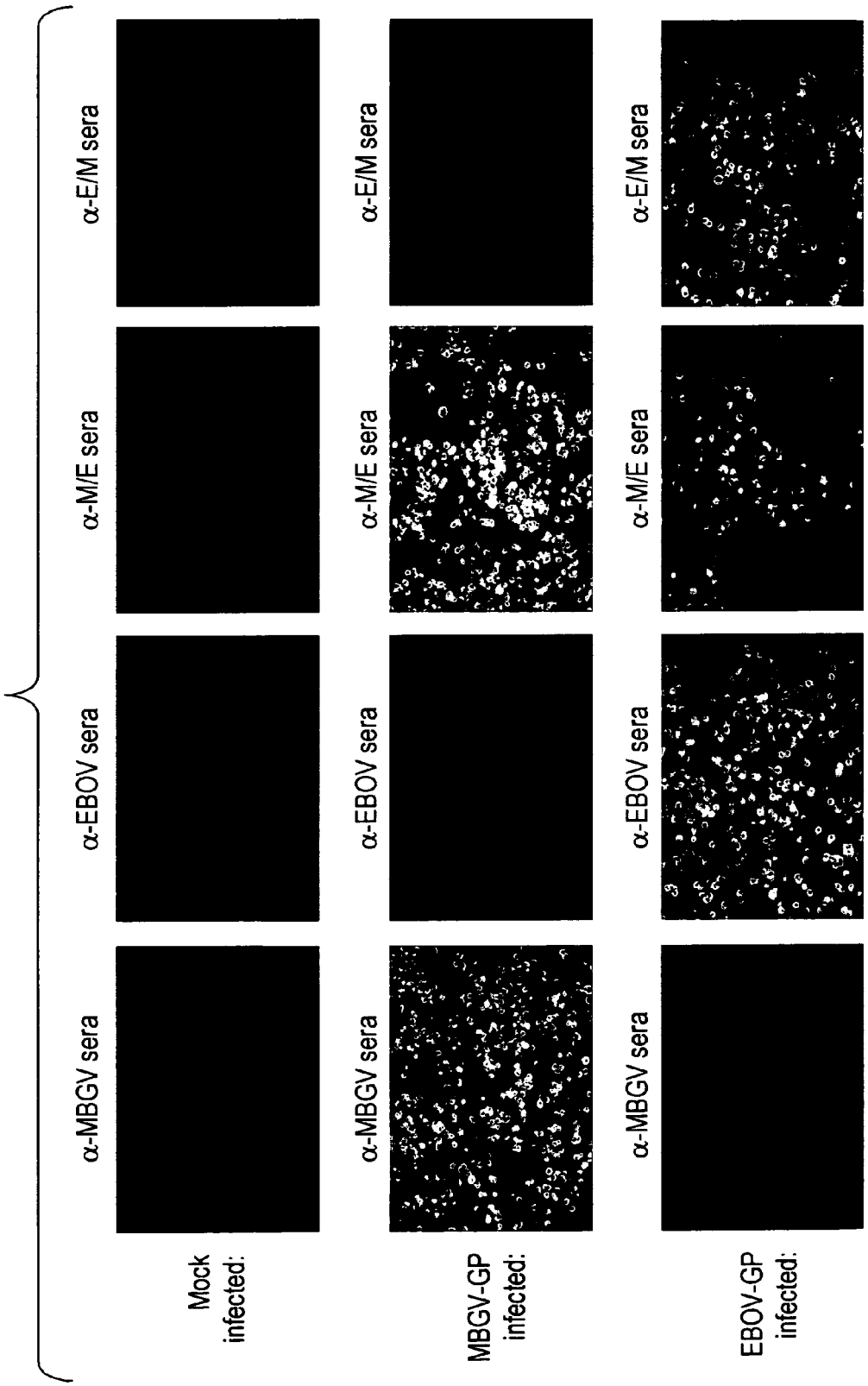
FIG. 10. Indirect immunofluoresence of Vero cells infected with VRPs expressing either no antigen (mock), M/M (MBGV-GP infected), or E/E (EBOV-GP infected). Antibodies used to detect MBGV or EBOV GP were either convalescent guinea pig sera from MBGV or EBOV infected guinea pigs (α-MBGV sera and α-EBOV sera), or sera from pre-challenge animals vaccinated with VRPs expressing M/E (α-M/E) or E/M (α-E/M sera) chimeras. EBOV-GP2 reactive antibodies were present in the M/E vaccinated animal sera; MBGV-GP2 specific antibodies in the E/M sera reacted at a very low, but detectable, level.

IFA was a third method used to detect the presence of either MBGV or EBOV GP2-specific antibodies in the vaccinated animals (FIG. 10). Cells mock infected or infected with VRPs expressing M/M, M/E, E/E, E/M were fixed onto teflon-etched spot slides, and stained with sera from E/M or M/E vaccinated pre-challenge animals. Convalescent E/E vaccinated, EBOV challenged and M/M vaccinated, MBGV challenged sera were used as controls. As a negative control, mock-infected cells did not react with any sera. Anti-MBGV sera detected M/M in infected cells but did not cross-react with E/E antigen; conversely anti-EBOV detected E/E protein but did not cross-react with M/M protein, as expected. Not surprisingly, anti-E/M sera detected E/E antigen, and M/E sera detected M/M antigen. Serum from M/E vaccinated animals did detected E/E antigen, suggesting the presence of anti-EBOV-GP2 specific antibodies. Serum from E/M vaccinated animals reacted, although very weakly, with cells expressing M/M protein. Thus, using this method both anti-EBOV-GP2 and anti-MBGV-GP2 reactive antibodies can be detected in serum from guinea pigs vaccinated with the chimeric GP proteins, although anti-MBGV-GP2 reactive antibodies were detected at a much lower level compared to the anti-EBOV-GP2-reactive antibodies In summary, wild-type MBGV and EBOV GP proteins were protective only against the virus from which they originated (type-specific immunity), as expected. However, chimeric MBGV/EBOV GP proteins were shown here to serve as dual-protective antigens in guinea pigs. In the context of a full-length (chimeric) GP, the MBGV-GP2 subunit was sufficient for protection against MBGV challenge in guinea pigs, and EBOV-GP2 protected 5/6 EBOV-challenged animals, suggesting that protective epitope(s) reside in the GP2 portion of the GP proteins. GP1 appeared to be the subunit most responsible for robust (sterile) immunity, as chimeras with the GP2 subunit homologous to challenge virus did not completely prevent viral replication in the vaccinated animal. Anti-GP2 antibody responses were subtle, but detectable with detergent-disrupted ELISA antigen, Western blot, or indirect immunofluoresence assay. Further studies to narrow down GP2-specific protective epitope(s) are underway using chimeras that have smaller segments within the GP2 subunit swapped between the EBOV and MBGV GP genes, and well as using the GP2 subunit alone as a vaccine antigen. Guinea pig T cell responses have not yet been evaluated for their role in mediating GP2-derived protection from lethal EBOV and MBGV challenge.

It remains to be determined what role the GP2-reactive antibodies play in mediating protection against lethal virus challenge for either EBOV or MBGV. While antibody titers have not been completely predictive of outcome of disease, nonetheless they are an important component of a protective immune response. Passive transfer of anti-GP antibodies has been shown to protect guinea pigs and mice from filovirus infection (Hevey et al., 1997, supra; Hevey et al., 2002, Vaccine 20, 586-593; Wilson et al., 2000, supra). However, T-cell responses are important in the immunoregulatory response to viral infections in general, and induction of a virus-specific CTL response is presumably an important component of immune protection against filoviruses. Indeed, Wilson et al. (2001, Cell. Mol. Life. Sci. 58, 1826-1841) showed that CTL response to EBOV NP was sufficient for protection against lethal EBOV challenge in mice. Presumably a combination of both cell-mediated and humoral immune response is necessary for protection and thus it is desirable to elicit both types of responses from any filovirus vaccine. The replicon delivery system used here elicits both antibody and cell-mediated immune responses, as antigen is produced from within host cells. The results presented here indicate that protective epitope(s) reside within the GP2 subunit of the MBGV GP protein and at least partially within the GP2 subunit of the EBOV GP protein. Further investigation into the protective mechanism of the replicon-expressed chimeric GPs is therefore warranted, in order to determine the nature of the protective epitope(s), whether based on conformational GP2 protein determinants, CTL response(s) to a particular GP2 epitope, so some combination therein. Additionally these results show that a construction of a single-component bivalent vaccine protective in guinea pigs against the two most divergent filoviruses, Ebola and Marburg, is achievable.

What is claimed is:

1. A recombinant DNA construct comprising:
   (i) a vector, and
   (ii) a DNA fragment encoding a chimeric filovirus protein comprising a full-length GP1 from a first filovirus fused to a full-length GP2 from a second filovirus, wherein the COOH-terminus of said GP1 is fused to the NH$_2$-terminus of GP2.

2. The recombinant DNA construct according to claim 1 wherein said DNA fragment encodes a chimeric protein chosen from the group consisting of:
   (i) Marburg Musoke GP1/Ebola Zaire GP2,
   (ii) Ebola Zaire GP1/Marbug Musoke GP2,
   (iii) Marburg Musoke GP1/Marburg Ravn GP2, and
   (iv) Marburg Ravn GP1/Marburg Musoke GP2.

3. A recombinant DNA construct according to claim 2, wherein said vector is an expression vector.

4. A recombinant DNA construct according to claim 2, wherein said vector is a prokaryotic vector.

5. A recombinant DNA construct according to claim 2, wherein said vector is a eukaryotic vector.

6. A recombinant DNA construct according to claim 2, wherein said vector is a VEE virus replicon vector.

7. The recombinant DNA construct according to claim 6 wherein said construct is EBOV-MAY GP1 (aa1-501)/MBGV-MUS GP2 (aa436-681).

8. The recombinant DNA construct according to claim 6 wherein said construct is MBGV-MUD GP1 (aa1-435)/EBOV-MAY GP2 (aa502-676).

9. The recombinant DNA construct according to claim 6 wherein said construct is MBGV-RVN GP1 (aa1-435)/MBGV-MUS GP2 (aa436-681).

10. The recombinant DNA construct according to claim 6 wherein said construct is MBGV-MUS GP1 (aa1-435)/MBGV-RVN GP2 (aa436-681).

11. Self replicating RNA produced from the construct of any of claims 6-10.

12. Infectious alphavirus particles produced from packaging the self replicating RNA of claim 11.

13. An isolated host cell transformed with a recombinant DNA construct according to claim 1.

14. A host cell according to claim 13 wherein said host cell is prokaryotic.

15. A host cell according to claim 13 wherein said host cell is eukaryotic.

16. A method for producing chimeric filovirus proteins comprising culturing the cells according to claim 14 under conditions such that said DNA fragment is expressed and said chimeric protein is produced and isolating said protein.

17. A method for producing chimeric filovirus proteins comprising culturing the cells according to claim 15 under conditions such that said DNA fragment is expressed and said chimeric protein is produced and isolating said protein.

18. A recombinant DNA vector according to claim 1 wherein said DNA fragment is SEQ ID NO:1.

19. A recombinant DNA vector according to claim 1 wherein said DNA fragment is SEQ ID NO:3.

20. A recombinant DNA vector according to claim 1 wherein said DNA fragment is SEQ ID NO:5.

21. A recombinant DNA vector according to claim 1 wherein said DNA fragment is SEQ ID NO:7.

22. An immunogenic composition comprising the infectious alphavirus particles of claim 12.

23. An isolated host cell transformed with a recombinant DNA construct according to claim 6.

24. The host cell of claim 23 wherein said host cell is prokaryotic.

25. The host cell of claim 23 wherein said host cell is eukaryotic.

26. An isolated host cell transformed with a recombinant DNA construct according to claim 7.

27. The host cell of claim 26 wherein said host cell is prokaryotic.

28. The host cell of claim 26 wherein said host cell is eukaryotic.

29. An isolated host cell transformed with a recombinant DNA construct according to claim 8.

30. The host cell of claim 29 wherein said host cell is prokaryotic.

31. The host cell of claim 29 wherein said host cell is eukaryotic.

32. An isolated host cell transformed with a recombinant DNA construct according to claim 9.

33. The host cell of claim 32 wherein said host cell is prokaryotic.

34. The host cell of claim 32 wherein said host cell is eukaryotic.

35. An isolated host cell transformed with a recombinant DNA construct according to claim 10.

36. The host cell of claim 35 wherein said host cell is prokaryotic.

37. The host cell of claim 35 wherein said host cell is eukaryotic.

* * * * *

SEQUENCE LISTING

<160> NUMBER OF SEQ ID NOS: 30

<210> SEQ ID NO 1
<211> LENGTH: 2252
<212> TYPE: DNA
<213> ORGANISM: Artificial Sequence
<220> FEATURE:
<223> OTHER INFORMATION: chimeric molecule between Ebola virus Zaire
      Mayinga strain Glycoprotein 1 and Marburg virus strain Musoke
      Glycoprotein 2

<400> SEQUENCE: 1

```
atgggcgtta caggaatatt gcagttacct cgtgatcgat tcaagaggac            50
atcattcttt ctttgggtaa ttatcctttt ccaaagaaca ttttccatcc           100
cacttggagt catccacaat agcacattac aggttagtga tgtcgacaaa           150
ctagtttgtc gtgacaaact gtcatccaca aatcaattga gatcagttgg           200
actgaatctc gaagggaatg gagtggcaac tgacgtgcca tctgcaacta           250
aaagatgggg cttcaggtcc ggtgtcccac caaaggtggt caattatgaa           300
gctggtgaat gggctgaaaa ctgctacaat cttgaaatca aaaaacctga           350
cgggagtgag tgtctaccag cagcgccaga cgggattcgg ggcttccccc           400
ggtgccggta tgtgcacaaa gtatcaggaa cgggaccgtg tgccggagac           450
tttgccttcc ataaagaggg tgctttcttc ctgtatgatc gacttgcttc           500
cacagttatc taccgaggaa cgactttcgc tgaaggtgtc gttgcatttc           550
tgatactgcc ccaagctaag aaggacttct tcagctcaca ccccttgaga           600
gagccggtca atgcaacgga ggacccgtct agtggctact attctaccac           650
aattagatat caggctaccg gttttggaac caatgagaca gagtacttgt           700
tcgaggttga caatttgacc tacgtccaac ttgaatcaag attcacacca           750
cagtttctgc tccagctgaa tgagacaata tatacaagtg ggaaaaggag           800
caataccacg ggaaaactaa tttggaaggt caaccccgaa attgatacaa           850
caatcgggga gtgggccttc tgggaaacta aaaaaaacct cactagaaaa           900
attcgcagtg aagagttgtc tttcacagtt gtatcaaacg gagccaaaaa           950
catcagtggt cagagtccgg cgcgaacttc ttccgaccca gggaccaaca          1000
caacaactga agaccacaaa atcatggctt cagaaaattc ctctgcaatg          1050
gttcaagtgc acagtcaagg aagggaagct gcagtgtcgc atctaacaac          1100
ccttgccaca atctccacga gtcccaatc cctcacaacc aaaccaggtc          1150
```

```
cggacaacag cacccataat acacccgtgt ataaacttga catctctgag    1200
gcaactcaag ttgaacaaca tcaccgcaga acagacaacg acagcacagc    1250
ctccgacact ccctctgcca cgaccgcagc cggaccccca aaagcagaga    1300
acaccaacac gagcaagagc actgacttcc tggaccccgc caccacaaca    1350
agtccccaaa accacagcga gaccgctggc aacaacaaca ctcatcacca    1400
agataccgga gaagagagtg ccagcagcgg gaagctaggc ttaattacca    1450
atactattgc tggagtcgca ggactgatca caggcgggag aagaactcga    1500
cgatcgatcc tctggaggga aggcgacatg ttcccttttc tggatgggtt    1550
aataaatgct ccaattgatt ttgacccagt tccaaataca aaaacaatct    1600
ttgatgaatc ctctagttct ggtgcctcgg ctgaggaaga tcaacatgcc    1650
tcccccaata ttagtttaac tttatcttat tttcctaata taaatgagaa    1700
cactgcctac tctggagaaa atgagaatga ttgtgatgca gagttaagaa    1750
tttggagcgt tcaggaggat gacctggccg cagggctcag ttggataccg    1800 tttttttggcc ctggaattga aggactttac actgctgttt taattaaaaa    1850
tcaaaacaat ttggtctgca ggttgaggcg tctagccaat caaactgcca    1900
aatccttgga actcttattg agagtcacaa ctgaggaaag aacattctcc    1950
ttaatcaata gacatgctat tgactttcta ctcacaagat ggggaggaac    2000
atgcaaagtg cttggacctg attgttgcat cgggatagaa gacttgtcca    2050
aaaatatttc agagcaaatt gaccaaatta aaaaggacga acaaaaagag    2100
gggactggtt ggggtctggg tggtaaatgg tggacatccg actggggtgt    2150
tcttactaac ttgggcattt tgctactatt atccatagct gtcttgattg    2200
ctctatcctg tatttgtcgt atctttacta aatatatcgg ataacggaat    2250
tc                                                        2252
```

<210> SEQ ID NO 2
<211> LENGTH: 747
<212> TYPE: PRT
<213> ORGANISM: Artificial Sequence
<220> FEATURE:
<223> OTHER INFORMATION: chimeric molecule between Ebola virus Zaire
    Mayinga strain Glycoprotein 1 and Marburg virus strain Musoke
    Glycoprotein 2

<400> SEQUENCE: 2

Met Gly Val Thr Gly Ile Leu Gln Leu Pro
 1               5                  10

Arg Asp Arg Phe Lys Arg Thr Ser Phe Phe
                15                  20

Leu Trp Val Ile Ile Leu Phe Gln Arg Thr
                25                  30

Phe Ser Ile Pro Leu Gly Val Ile His Asn
                35                  40

Ser Thr Leu Gln Val Ser Asp Val Asp Lys
                45                  50

Leu Val Cys Arg Asp Lys Leu Ser Ser Thr
                55                  60

Asn Gln Leu Arg Ser Val Gly Leu Asn Leu
                65                  70

```
Glu Gly Asn Gly Val Ala Thr Asp Val Pro
                75                  80

Ser Ala Thr Lys Arg Trp Gly Phe Arg Ser
                85                  90

Gly Val Pro Pro Lys Val Val Asn Tyr Glu
                95                 100

Ala Gly Glu Trp Ala Glu Asn Cys Tyr Asn
               105                 110

Leu Glu Ile Lys Lys Pro Asp Gly Ser Glu
               115                 120

Cys Leu Pro Ala Ala Pro Asp Gly Ile Arg
               125                 130

Gly Phe Pro Arg Cys Arg Tyr Val His Lys
               135                 140

Val Ser Gly Thr Gly Pro Cys Ala Gly Asp
               145                 150

Phe Ala Phe His Lys Glu Gly Ala Phe Phe
               155                 160

Leu Tyr Asp Arg Leu Ala Ser Thr Val Ile
               165                 170

Tyr Arg Gly Thr Thr Phe Ala Glu Gly Val
               175                 180

Val Ala Phe Leu Ile Leu Pro Gln Ala Lys
               185                 190

Lys Asp Phe Phe Ser Ser His Pro Leu Arg
               195                 200

Glu Pro Val Asn Ala Thr Glu Asp Pro Ser
               205                 210

Ser Gly Tyr Tyr Ser Thr Thr Ile Arg Tyr
               215                 220

Gln Ala Thr Gly Phe Gly Thr Asn Glu Thr
               225                 230

Glu Tyr Leu Phe Glu Val Asp Asn Leu Thr
               235                 240

Tyr Val Gln Leu Glu Ser Arg Phe Thr Pro
               245                 250

Gln Phe Leu Leu Gln Leu Asn Glu Thr Ile
               255                 260

Tyr Thr Ser Gly Lys Arg Ser Asn Thr Thr
               265                 270

Gly Lys Leu Ile Trp Lys Val Asn Pro Glu
               275                 280

Ile Asp Thr Thr Ile Gly Glu Trp Ala Phe
               285                 290

Trp Glu Thr Lys Lys Asn Leu Thr Arg Lys
               295                 300

Ile Arg Ser Glu Glu Leu Ser Phe Thr Val
               305                 310

Val Ser Asn Gly Ala Lys Asn Ile Ser Gly
               315                 320

Gln Ser Pro Ala Arg Thr Ser Ser Asp Pro
               325                 330

Gly Thr Asn Thr Thr Thr Glu Asp His Lys
```

```
                    335                 340
Ile Met Ala Ser Glu Asn Ser Ser Ala Met
                345                 350
Val Gln Val His Ser Gln Gly Arg Glu Ala
                355                 360
Ala Val Ser His Leu Thr Thr Leu Ala Thr
                365                 370
Ile Ser Thr Ser Pro Gln Ser Leu Thr Thr
                375                 380
Lys Pro Gly Pro Asp Asn Ser Thr His Asn
                385                 390
Thr Pro Val Tyr Lys Leu Asp Ile Ser Glu
                395                 400
Ala Thr Gln Val Glu Gln His His Arg Arg
                405                 410
Thr Asp Asn Asp Ser Thr Ala Ser Asp Thr
                415                 420
Pro Ser Ala Thr Thr Ala Ala Gly Pro Pro
                425                 430
Lys Ala Glu Asn Thr Asn Thr Ser Lys Ser
                435                 440
Thr Asp Phe Leu Asp Pro Ala Thr Thr Thr
                445                 450
Ser Pro Gln Asn His Ser Glu Thr Ala Gly
                455                 460
Asn Asn Asn Thr His His Gln Asp Thr Gly
                465                 470
Glu Glu Ser Ala Ser Ser Gly Lys Leu Gly
                475                 480
Leu Ile Thr Asn Thr Ile Ala Gly Val Ala
                485                 490
Gly Leu Ile Thr Gly Gly Arg Arg Thr Arg
                495                 500
Arg Ser Ile Leu Trp Arg Glu Gly Asp Met
                505                 510
Phe Pro Phe Leu Asp Gly Leu Ile Asn Ala
                515                 520
Pro Ile Asp Phe Asp Pro Val Pro Asn Thr
                525                 530
Lys Thr Ile Phe Asp Glu Ser Ser Ser Ser
                535                 540
Gly Ala Ser Ala Glu Glu Asp Gln His Ala
                545                 550
Ser Pro Asn Ile Ser Leu Thr Leu Ser Tyr
                555                 560
Phe Pro Asn Ile Asn Glu Asn Thr Ala Tyr
                565                 570
Ser Gly Glu Asn Glu Asn Asp Cys Asp Ala
                575                 580
Glu Leu Arg Ile Trp Ser Val Gln Glu Asp
                585                 590
Asp Leu Ala Ala Gly Leu Ser Trp Ile Pro
                595                 600
```

```
Phe Phe Gly Pro Gly Ile Glu Gly Leu Tyr
            605                 610

Thr Ala Val Leu Ile Lys Asn Gln Asn Asn
            615                 620

Leu Val Cys Arg Leu Arg Arg Leu Ala Asn
            625                 630

Gln Thr Ala Lys Ser Leu Glu Leu Leu Leu
            635                 640

Arg Val Thr Thr Glu Glu Arg Thr Phe Ser
            645                 650

Leu Ile Asn Arg His Ala Ile Asp Phe Leu
            655                 660

Leu Thr Arg Trp Gly Gly Thr Cys Lys Val
            665                 670

Leu Gly Pro Asp Cys Cys Ile Gly Ile Glu
            675                 680

Asp Leu Ser Lys Asn Ile Ser Glu Gln Ile
            685                 690

Asp Gln Ile Lys Lys Asp Glu Gln Lys Glu
            695                 700

Gly Thr Gly Trp Gly Leu Gly Gly Lys Trp
            705                 710

Trp Thr Ser Asp Trp Gly Val Leu Thr Asn
            715                 720

Leu Gly Ile Leu Leu Leu Leu Ser Ile Ala
            725                 730

Val Leu Ile Ala Leu Ser Cys Ile Cys Arg
            735                 740

Ile Phe Thr Lys Tyr Ile Gly
            745

<210> SEQ ID NO 3
<211> LENGTH: 1841
<212> TYPE: DNA
<213> ORGANISM: Artificial Sequence
<220> FEATURE:
<223> OTHER INFORMATION: chimeric molecule between Marburg virus strain
      Musoke Glycoprotein 1 and Ebola virus Zaire Mayinga strain
      Glycoprotein 2

<400> SEQUENCE: 3
atgaagacca catgtttcct tatcagtctt atcttaattc aagggacaaa         50
aaatctcccc attttagaga tagctagtaa taatcaaccc caaaatgtgg        100
attcggtatg ctccggaact ctccagaaga cagaagacgt ccatctgatg        150
ggattcacac tgagtgggca aaaagttgct gattcccctt ggaggcatc         200 caagcgatgg gctttcagga caggtgtacc tcccaagaat gttgagtaca        250
cagaggggga ggaagccaaa acatgctaca atataagtgt aacggatccc        300
tctggaaaat ccttgctgtt agatcctcct accaacatcc gtgactatcc        350
gaaatgcaaa actatccatc atattcaagg tcaaaaccct catgcacagg        400
ggatcgccct tcatttatgg ggagcatttt ttctgtatga tcgcattgcc        450
tccacaacaa tgtaccgagg caaagtcttc actgaaggga catagcagc         500 tatgattgtc aataagacag tgcacaaaat gattttctcg cggcaaggac        550
```

-continued

```
aagggtaccg tcatatgaat ctgacttcta ctaataaata ttggacaagt        600
agtaacggaa cgcaaacgaa tgacactgga tgtttcggcg ctcttcaaga        650
atacaattct acaaagaacc aaacatgtgc tccgtccaaa atacctccac        700
cactgcccac agcccgtccg agatcaaac tcacaagcac cccaactgat         750
gccaccaaac tcaataccac ggacccaagc agtgatgatg aggacctcgc        800
aacatccggc tcagggtccg agaacgaga accccacaca acttctgatg         850
cggtcaccaa gcaagggctt tcatcaacaa tgccacccac tccctcacca        900
caaccaagca cgccacagca aggaggaaac aacacaaacc attcccaaga        950
tgctgtgact gaactagaca aaataaacac aactgcacaa ccgtccatgc        1000 ccctcataa cactaccaca atctctacta acaacacctc caaacacaac         1050
ttcagcactc tctctgcacc attacaaaac accaccaatg acaacacaca        1100
gagcacaatc actgaaaatg agcaaaccag tgcccctcg ataacaaccc         1150 tgcctccaac gggaaatccc accacagcaa agagcaccag cagcaaaaaa        1200
ggccccgcca caacggcacc aaacacgaca atgagcatt tcaccagtcc         1250 tccccccacc cccagctcga ctgcacaaca tcttgtatat ttcagaagaa        1300
agcgatcggc aattgtcaat gctcaaccca atgcaaccc taatttacat         1350 tactggacta ctcaggatga aggtgctgca atcggactgg cctggatacc        1400
atatttcggg ccagcagccg agggaattta catagagggg ctaatgcaca        1450
atcaagatgg tttaatctgt gggttgagac agctggccaa cgagacgact        1500
caagctcttc aactgttcct gagagccaca actgagctac gcaccttttc        1550
aatcctcaac cgtaaggcaa ttgatttctt gctgcagcga tggggcggca        1600
catgccacat tctgggaccg gactgctgta tcgaaccaca tgattggacc        1650
aagaacataa cagacaaaat tgatcagatt attcatgatt tgttgataa         1700 aacccttccg gaccaggggg acaatgacaa ttggtggaca ggatggagac        1750
aatggatacc ggcaggtatt ggagttacag gcgttataat tgcagttatc        1800
gctttattct gtatatgcaa atttgtcttt tagttgaatt c                 1841
```

<210> SEQ ID NO 4
<211> LENGTH: 610
<212> TYPE: PRT
<213> ORGANISM: Artificial Sequence
<220> FEATURE:
<223> OTHER INFORMATION: chimeric molecule between Marburg virus strain
    Musoke Glycoprotein 1 and Ebola virus Zaire Mayinga strain
    Glycoprotein 2

<400> SEQUENCE: 4

Met Lys Thr Thr Cys Phe Leu Ile Ser Leu
1               5                   10

Ile Leu Ile Gln Gly Thr Lys Asn Leu Pro
            15                  20

Ile Leu Glu Ile Ala Ser Asn Asn Gln Pro
            25                  30

Gln Asn Val Asp Ser Val Cys Ser Gly Thr
            35                  40

Leu Gln Lys Thr Glu Asp Val His Leu Met
            45                  50

```
Gly Phe Thr Leu Ser Gly Gln Lys Val Ala
                55                  60

Asp Ser Pro Leu Glu Ala Ser Lys Arg Trp
                65                  70

Ala Phe Arg Thr Gly Val Pro Pro Lys Asn
                75                  80

Val Glu Tyr Thr Glu Gly Glu Glu Ala Lys
                85                  90

Thr Cys Tyr Asn Ile Ser Val Thr Asp Pro
                95                 100

Ser Gly Lys Ser Leu Leu Leu Asp Pro Pro
               105                 110

Thr Asn Ile Arg Asp Tyr Pro Lys Cys Lys
               115                 120

Thr Ile His His Ile Gln Gly Gln Asn Pro
               125                 130

His Ala Gln Gly Ile Ala Leu His Leu Trp
               135                 140

Gly Ala Phe Phe Leu Tyr Asp Arg Ile Ala
               145                 150

Ser Thr Thr Met Tyr Arg Gly Lys Val Phe
               155                 160

Thr Glu Gly Asn Ile Ala Ala Met Ile Val
               165                 170

Asn Lys Thr Val His Lys Met Ile Phe Ser
               175                 180

Arg Gln Gly Gln Gly Tyr Arg His Met Asn
               185                 190

Leu Thr Ser Thr Asn Lys Tyr Trp Thr Ser
               195                 200

Ser Asn Gly Thr Gln Thr Asn Asp Thr Gly
               205                 210

Cys Phe Gly Ala Leu Gln Glu Tyr Asn Ser
               215                 220

Thr Lys Asn Gln Thr Cys Ala Pro Ser Lys
               225                 230

Ile Pro Pro Pro Leu Pro Thr Ala Arg Pro
               235                 240

Glu Ile Lys Leu Thr Ser Thr Pro Thr Asp
               245                 250

Ala Thr Lys Leu Asn Thr Thr Asp Pro Ser
               255                 260

Ser Asp Asp Glu Asp Leu Ala Thr Ser Gly
               265                 270

Ser Gly Ser Gly Glu Arg Glu Pro His Thr
               275                 280

Thr Ser Asp Ala Val Thr Lys Gln Gly Leu
               285                 290

Ser Ser Thr Met Pro Pro Thr Pro Ser Pro
               295                 300

Gln Pro Ser Thr Pro Gln Gln Gly Gly Asn
               305                 310
```

```
Asn Thr Asn His Ser Gln Asp Ala Val Thr
            315                 320

Glu Leu Asp Lys Asn Asn Thr Thr Ala Gln
            325                 330

Pro Ser Met Pro Pro His Asn Thr Thr Thr
            335                 340

Ile Ser Thr Asn Asn Thr Ser Lys His Asn
            345                 350

Phe Ser Thr Leu Ser Ala Pro Leu Gln Asn
            355                 360

Thr Thr Asn Asp Asn Thr Gln Ser Thr Ile
            365                 370

Thr Glu Asn Glu Gln Thr Ser Ala Pro Ser
            375                 380

Ile Thr Thr Leu Pro Pro Thr Gly Asn Pro
            385                 390

Thr Thr Ala Lys Ser Thr Ser Ser Lys Lys
            395                 400

Gly Pro Ala Thr Thr Ala Pro Asn Thr Thr
            405                 410

Asn Glu His Phe Thr Ser Pro Pro Pro Thr
            415                 420

Pro Ser Ser Thr Ala Gln His Leu Val Tyr
            425                 430

Phe Arg Arg Lys Arg Ser Ala Ile Val Asn
            435                 440

Ala Gln Pro Lys Cys Asn Pro Asn Leu His
            445                 450

Tyr Trp Thr Thr Gln Asp Glu Gly Ala Ala
            455                 460

Ile Gly Leu Ala Trp Ile Pro Tyr Phe Gly
            465                 470

Pro Ala Ala Glu Gly Ile Tyr Ile Glu Gly
            475                 480

Leu Met His Asn Gln Asp Gly Leu Ile Cys
            485                 490

Gly Leu Arg Gln Leu Ala Asn Glu Thr Thr
            495                 500

Gln Ala Leu Gln Leu Phe Leu Arg Ala Thr
            505                 510

Thr Glu Leu Arg Thr Phe Ser Ile Leu Asn
            515                 520

Arg Lys Ala Ile Asp Phe Leu Leu Gln Arg
            525                 530

Trp Gly Gly Thr Cys His Ile Leu Gly Pro
            535                 540

Asp Cys Cys Ile Glu Pro His Asp Trp Thr
            545                 550

Lys Asn Ile Thr Asp Lys Ile Asp Gln Ile
            555                 560

Ile His Asp Phe Val Asp Lys Thr Leu Pro
            565                 570

Asp Gln Gly Asp Asn Asp Asn Trp Trp Thr
```

```
                575                 580
Gly Trp Arg Gln Trp Ile Pro Ala Gly Ile
            585                 590

Gly Val Thr Gly Val Ile Ile Ala Val Ile
            595                 600

Ala Leu Phe Cys Ile Cys Lys Phe Val Phe
            605                 610

<210> SEQ ID NO 5
<211> LENGTH: 2046
<212> TYPE: DNA
<213> ORGANISM: Artificial Sequence
<220> FEATURE:
<223> OTHER INFORMATION: chimeric molecule between Marburg virus strain
      Musoke Glycoprotein 1 and Marburg virus strain Raven Glycoprotein
      2

<400> SEQUENCE: 5
atgaagacca catgtttcct tatcagtctt atcttaattc aagggacaaa          50
aaatctcccc attttagaga tagctagtaa taatcaaccc caaaatgtgg         100
attcggtatg ctccggaact ctccagaaga cagaagacgt ccatctgatg         150
ggattcacac tgagtgggca aaaagttgct gattccccctt tggaggcatc        200 caagcgatgg gctttcagga caggtgtacc tcccaagaat gttgagtaca         250
cagaggggga ggaagccaaa acatgctaca atataagtgt aacggatccc         300
tctggaaaat ccttgctgtt agatcctcct accaacatcc gtgactatcc         350
gaaatgcaaa actatccatc atattcaagg tcaaaaccct catgcacagg         400
ggatcgccct tcatttatgg ggagcatttt ttctgtatga tcgcattgcc         450
tccacaacaa tgtaccgagg caaagtcttc actgaaggga acatagcagc         500
tatgattgtc aataagacag tgcacaaaat gattttctcg cggcaaggac         550
aagggtaccg tcatatgaat ctgacttcta ctaataaata ttggacaagt         600
agtaacggaa cgcaaacgaa tgacactgga tgtttcggcg ctcttcaaga         650
atacaattct acaaagaacc aaacatgtgc tccgtccaaa atacctccac         700
cactgcccac agcccgtccg agatcaaact cacaagcac cccaactgat          750 gccaccaaac tcaataccac ggacccaagc agtgatgatg aggacctcgc         800
aacatccggc tcagggtccg agaacgaga ccccacaca acttctgatg           850 cggtcaccaa gcaagggctt tcatcaacaa tgccaccccac tccctcacca        900 caaccaagca cgccacagca aggaggaaac aacacaaacc attcccaaga         950
tgctgtgact gaactagaca aaaataacac aactgcacaa ccgtccatgc        1000
cccctcataa cactaccaca atctctacta caacacctc caaacacaac         1050 ttcagcactc tctctgcacc attacaaaac accaccaatg acaacacaca        1100
gagcacaatc actgaaaatg agcaaaccag tgcccctcg ataacaaccc         1150 tgcctccaac gggaaatccc accacagcaa agagcaccag cagcaaaaaa        1200
ggccccgcca aacggcacc aaacacgaca aatgagcatt tcaccagtcc         1250
tcccccaacc cccagctcga ctgcacaaca tcttgtatat tcagaagaa          1300 agcgatcgat ttctggaaaa gaaggtgata tattcccgtt tttagatggg        1350
ttaataaata ctgaaattga ttttgatcca atcccaaaca cagaaacaat        1400
```

| | |
|---|---|
| ctttgatgaa tctcccagct ttaatacttc aactaatgag gaacaacaca | 1450 |
| ctcccccgaa tatcagttta actttctctt attttcctga taaaaatgga | 1500 |
| gatactgcct actctgggga aaacgagaat gattgtgatg cagagttgag | 1550 |
| gatttggagt gtgcaggagg acgatttggc ggcagggctt agctggatac | 1600 |
| cattttttgg ccctggaatc gaaggactct atactgccgg tttaatcaaa | 1650 |
| aatcagaaca atttagtttg taggttgagg cgcttagcta atcaaactgc | 1700 |
| taaatccttg gagctcttgt taagggtcac aaccgaggaa aggacatttt | 1750 |
| ccttaatcaa taggcatgca attgactttt tgcttacgag gtggggcgga | 1800 |
| acatgcaagg tgctaggacc tgattgttgc ataggaatag aagatctatc | 1850 |
| taaaatatc tcagaacaaa tcgacaaaat cagaaaggat gaacaaaagg | 1900 |
| aggaaactgg ctggggtcta ggtggcaaat ggtggacatc tgactggggt | 1950 |
| gttctcacca atttgggcat cctgctacta ttatctatag ctgttctgat | 2000 |
| tgctctgtcc tgtatctgtc gtatcttcac taaatacatt ggatga | 2046 |

<210> SEQ ID NO 6
<211> LENGTH: 681
<212> TYPE: PRT
<213> ORGANISM: Artificial Sequence
<220> FEATURE:
<223> OTHER INFORMATION: chimeric molecule between Marburg virus strain
      Musoke Glycoprotein 1 and Marburg virus strain Raven Glycoprotein
      2

<400> SEQUENCE: 6

Met Lys Thr Thr Cys Phe Leu Ile Ser Leu
 1               5                  10

Ile Leu Ile Gln Gly Thr Lys Asn Leu Pro
             15                  20

Ile Leu Glu Ile Ala Ser Asn Asn Gln Pro
             25                  30

Gln Asn Val Asp Ser Val Cys Ser Gly Thr
             35                  40

Leu Gln Lys Thr Glu Asp Val His Leu Met
             45                  50

Gly Phe Thr Leu Ser Gly Gln Lys Val Ala
             55                  60

Asp Ser Pro Leu Glu Ala Ser Lys Arg Trp
             65                  70

Ala Phe Arg Thr Gly Val Pro Pro Lys Asn
             75                  80

Val Glu Tyr Thr Glu Gly Glu Glu Ala Lys
             85                  90

Thr Cys Tyr Asn Ile Ser Val Thr Asp Pro
             95                 100

Ser Gly Lys Ser Leu Leu Leu Asp Pro Pro
            105                 110

Thr Asn Ile Arg Asp Tyr Pro Lys Cys Lys
            115                 120

Thr Ile His His Ile Gln Gly Gln Asn Pro
            125                 130

His Ala Gln Gly Ile Ala Leu His Leu Trp
            135                 140

```
Gly Ala Phe Phe Leu Tyr Asp Arg Ile Ala
                145                 150

Ser Thr Thr Met Tyr Arg Gly Lys Val Phe
                155                 160

Thr Glu Gly Asn Ile Ala Ala Met Ile Val
                165                 170

Asn Lys Thr Val His Lys Met Ile Phe Ser
                175                 180

Arg Gln Gly Gln Gly Tyr Arg His Met Asn
                185                 190

Leu Thr Ser Thr Asn Lys Tyr Trp Thr Ser
                195                 200

Ser Asn Gly Thr Gln Thr Asn Asp Thr Gly
                205                 210

Cys Phe Gly Ala Leu Gln Glu Tyr Asn Ser
                215                 220

Thr Lys Asn Gln Thr Cys Ala Pro Ser Lys
                225                 230

Ile Pro Pro Pro Leu Pro Thr Ala Arg Pro
                235                 240

Glu Ile Lys Leu Thr Ser Thr Pro Thr Asp
                245                 250

Ala Thr Lys Leu Asn Thr Thr Asp Pro Ser
                255                 260

Ser Asp Asp Glu Asp Leu Ala Thr Ser Gly
                265                 270

Ser Gly Ser Gly Glu Arg Glu Pro His Thr
                275                 280

Thr Ser Asp Ala Val Thr Lys Gln Gly Leu
                285                 290

Ser Ser Thr Met Pro Pro Thr Pro Ser Pro
                295                 300

Gln Pro Ser Thr Pro Gln Gln Gly Gly Asn
                305                 310

Asn Thr Asn His Ser Gln Asp Ala Val Thr
                315                 320

Glu Leu Asp Lys Asn Asn Thr Thr Ala Gln
                325                 330

Pro Ser Met Pro Pro His Asn Thr Thr Thr
                335                 340

Ile Ser Thr Asn Asn Thr Ser Lys His Asn
                345                 350

Phe Ser Thr Leu Ser Ala Pro Leu Gln Asn
                355                 360

Thr Thr Asn Asp Asn Thr Gln Ser Thr Ile
                365                 370

Thr Glu Asn Glu Gln Thr Ser Ala Pro Ser
                375                 380

Ile Thr Thr Leu Pro Pro Thr Gly Asn Pro
                385                 390

Thr Thr Ala Lys Ser Thr Ser Ser Lys Lys
                395                 400
```

-continued

```
Gly Pro Ala Thr Thr Ala Pro Asn Thr Thr
                405                 410

Asn Glu His Phe Thr Ser Pro Pro Thr
                415                 420

Pro Ser Ser Thr Ala Gln His Leu Val Tyr
                425                 430

Phe Arg Arg Lys Arg Ser Ile Phe Trp Lys
                435                 440

Glu Gly Asp Ile Phe Pro Phe Leu Asp Gly
                445                 450

Leu Ile Asn Thr Glu Ile Asp Phe Asp Pro
                455                 460

Ile Pro Asn Thr Glu Thr Ile Phe Asp Glu
                465                 470

Ser Pro Ser Phe Asn Thr Ser Thr Asn Glu
                475                 480

Glu Gln His Thr Pro Pro Asn Ile Ser Leu
                485                 490

Thr Phe Ser Tyr Phe Pro Asp Lys Asn Gly
                495                 500

Asp Thr Ala Tyr Ser Gly Glu Asn Glu Asn
                505                 510

Asp Cys Asp Ala Glu Leu Arg Ile Trp Ser
                515                 520

Val Gln Glu Asp Asp Leu Ala Ala Gly Leu
                525                 530

Ser Trp Ile Pro Phe Phe Gly Pro Gly Ile
                535                 540

Glu Gly Leu Tyr Thr Ala Gly Leu Ile Lys
                545                 550

Asn Gln Asn Asn Leu Val Cys Arg Leu Arg
                555                 560

Arg Leu Ala Asn Gln Thr Ala Lys Ser Leu
                565                 570

Glu Leu Leu Leu Arg Val Thr Thr Glu Glu
                575                 580

Arg Thr Phe Ser Leu Ile Asn Arg His Ala
                585                 590

Ile Asp Phe Leu Leu Thr Arg Trp Gly Gly
                595                 600

Thr Cys Lys Val Leu Gly Pro Asp Cys Cys
                605                 610

Ile Gly Ile Glu Asp Leu Ser Lys Asn Ile
                615                 620

Ser Glu Gln Ile Asp Lys Ile Arg Lys Asp
                625                 630

Glu Gln Lys Glu Glu Thr Gly Trp Gly Leu
                635                 640

Gly Gly Lys Trp Trp Thr Ser Asp Trp Gly
                645                 650

Val Leu Thr Asn Leu Gly Ile Leu Leu Leu
                655                 660

Leu Ser Ile Ala Val Leu Ile Ala Leu Ser
```

```
                    665                 670
Cys Ile Cys Arg Ile Phe Thr Lys Tyr Ile
                    675                 680

Gly

<210> SEQ ID NO 7
<211> LENGTH: 2046
<212> TYPE: DNA
<213> ORGANISM: Artificial Sequence
<220> FEATURE:
<223> OTHER INFORMATION: chimeric molecule between Marburg virus strain
      Raven Glycoprotein 1 and Marburg virus strain Musoke Glycoprotein
      2

<400> SEQUENCE: 7
atgaagacca tatattttct gattagtctc attttaatcc aaagtataaa              50
aactctccct gttttagaaa ttgctagtaa cagccaacct caagatgtag             100
attcagtgtg ctccggaacc tccaaaaga cagaagatgt tcatctgatg              150
ggatttacac tgagtgggca aaaagttgct gattcccctt ggaagcatc              200 taaacgatgg gctttcagga caggtgttcc tcccaagaac gttgagtata             250
cggaaggaga agaagccaaa acatgttaca atataagtgt aacagaccct             300
tctggaaaat ccttgctgct ggatcctccc agtaatatcc gcgattaccc             350
taaatgtaaa actgttcatc atattcaagg tcaaaaccct catgcacagg             400
ggattgccct ccatttgtgg ggggcatttt tcttgtatga tcgcgttgcc             450
tctacaacaa tgtaccgagg caaggtcttc actgaaggaa atatagcagc              500
tatgattgtt aataagacag ttcacagaat gattttttct aggcaaggac             550
aaggttatcg tcacatgaac ttgacctcca ccaataaata ttggacaagc             600
agcaatgaaa cgcagagaaa tgatacggga tgttttggca tcctccaaga             650
atacaactcc acaaacaatc aaacatgccc tccatctctt aaacctccat              700
ccctgcccac agtaactccg agcattcact ctacaaatac tcaaattaat             750
actgctaaat ctggaactat gaacccaagt agcgacgatg aggaccttat              800
gatttccggc tcaggatctg gagaacaggg gccccacaca actcttaatg             850
tagtcactga acagaaacaa tcgtcaacaa tattgtccac tccttcacta              900
catccaagca cctcacaaca tgagcaaaac agtacgaatc cttcccgaca             950
tgctgtaact gagcacaatg gaaccgaccc aacaacacaa ccagcaacgc            1000
tcctcaacaa tactaataca actcccacct ataacactct caagtacaac            1050
ctcagtactc cttcccctcc aacccgcaac atcaccaata atgatacaca            1100
acgtgaacta gcagaaagcg aacaaaccaa tgctcagttg aacacaactc            1150
tagatccaac agaaaatccc accacaggac aagacaccaa cagcacaacc            1200
aacatcatca tgacgacatc agatataaca agcaaacacc ccacaaattc            1250
ttctccggat tctagtccga caacccgccc tcctatatac tttagaaaga            1300
aacgatcgat cctctggagg gaaggcgaca tgttccctt tctggatggg             1350 ttaataaatg ctccaattga ttttgaccca gttccaaata caaaaacaat            1400 cttgatgaa tcctctagtt ctggtgcctc ggctgaggaa gatcaacatg             1450
cctcccccaa tattagttta actttatctt attttcctaa tataaatgag            1500
```

-continued

```
aacactgcct actctggaga aaatgagaat gattgtgatg cagagttaag      1550
aatttggagc gttcaggagg atgacctggc cgcagggctc agttggatac      1600
cgttttttgg ccctggaatt gaaggacttt acactgctgt tttaattaaa      1650
aatcaaaaca atttggtctg caggttgagg cgtctagcca atcaaactgc      1700
caaatccttg gaactcttat tgagagtcac aactgaggaa agaacattct      1750
ccttaatcaa tagacatgct attgactttc tactcacaag atggggagga      1800
acatgcaaag tgcttggacc tgattgttgc atcgggatag aagacttgtc      1850 caaaatatt tcagagcaaa ttgaccaaat taaaaaggac gaacaaaaag       1900
aggggactgg ttggggtctg ggtggtaaat ggtggacatc cgactggggt      1950
gttcttacta acttgggcat tttgctacta ttatccatag ctgtcttgat      2000
tgctctatcc tgtatttgtc gtatctttac taaatatatc ggataa         2046
```

<210> SEQ ID NO 8
<211> LENGTH: 681
<212> TYPE: PRT
<213> ORGANISM: Artificial Sequence
<220> FEATURE:
<223> OTHER INFORMATION: chimeric molecule between Marburg virus strain Raven Glycoprotein 1 and Marburg virus strain Musoke Glycoprotein 2

<400> SEQUENCE: 8

```
Met Lys Thr Ile Tyr Phe Leu Ile Ser Leu
 1               5                  10

Ile Leu Ile Gln Ser Ile Lys Thr Leu Pro
            15                     20

Val Leu Glu Ile Ala Ser Asn Ser Gln Pro
            25                     30

Gln Asp Val Asp Ser Val Cys Ser Gly Thr
            35                     40

Leu Gln Lys Thr Glu Asp Val His Leu Met
            45                     50

Gly Phe Thr Leu Ser Gly Gln Lys Val Ala
            55                     60

Asp Ser Pro Leu Glu Ala Ser Lys Arg Trp
            65                     70

Ala Phe Arg Thr Gly Val Pro Pro Lys Asn
            75                     80

Val Glu Tyr Thr Glu Gly Glu Glu Ala Lys
            85                     90

Thr Cys Tyr Asn Ile Ser Val Thr Asp Pro
            95                    100

Ser Gly Lys Ser Leu Leu Leu Asp Pro Pro
           105                    110

Ser Asn Ile Arg Asp Tyr Pro Lys Cys Lys
           115                    120

Thr Val His His Ile Gln Gly Gln Asn Pro
           125                    130

His Ala Gln Gly Ile Ala Leu His Leu Trp
           135                    140

Gly Ala Phe Phe Leu Tyr Asp Arg Val Ala
           145                    150
```

```
Ser Thr Thr Met Tyr Arg Gly Lys Val Phe
            155                 160

Thr Glu Gly Asn Ile Ala Ala Met Ile Val
            165                 170

Asn Lys Thr Val His Arg Met Ile Phe Ser
            175                 180

Arg Gln Gly Gln Gly Tyr Arg His Met Asn
            185                 190

Leu Thr Ser Thr Asn Lys Tyr Trp Thr Ser
            195                 200

Ser Asn Glu Thr Gln Arg Asn Asp Thr Gly
            205                 210

Cys Phe Gly Ile Leu Gln Glu Tyr Asn Ser
            215                 220

Thr Asn Asn Gln Thr Cys Pro Pro Ser Leu
            225                 230

Lys Pro Pro Ser Leu Pro Thr Val Thr Pro
            235                 240

Ser Ile His Ser Thr Asn Thr Gln Ile Asn
            245                 250

Thr Ala Lys Ser Gly Thr Met Asn Pro Ser
            255                 260

Ser Asp Asp Glu Asp Leu Met Ile Ser Gly
            265                 270

Ser Gly Ser Gly Glu Gln Gly Pro His Thr
            275                 280

Thr Leu Asn Val Val Thr Glu Gln Lys Gln
            285                 290

Ser Ser Thr Ile Leu Ser Thr Pro Ser Leu
            295                 300

His Pro Ser Thr Ser Gln His Glu Gln Asn
            305                 310

Ser Thr Asn Pro Ser Arg His Ala Val Thr
            315                 320

Glu His Asn Gly Thr Asp Pro Thr Thr Gln
            325                 330

Pro Ala Thr Leu Leu Asn Asn Thr Asn Thr
            335                 340

Thr Pro Thr Tyr Asn Thr Leu Lys Tyr Asn
            345                 350

Leu Ser Thr Pro Ser Pro Thr Arg Asn
            355                 360

Ile Thr Asn Asn Asp Thr Gln Arg Glu Leu
            365                 370

Ala Glu Ser Glu Gln Thr Asn Ala Gln Leu
            375                 380

Asn Thr Thr Leu Asp Pro Thr Glu Asn Pro
            385                 390

Thr Thr Gly Gln Asp Thr Asn Ser Thr Thr
            395                 400

Asn Ile Ile Met Thr Thr Ser Asp Ile Thr
            405                 410

Ser Lys His Pro Thr Asn Ser Ser Pro Asp
```

```
                        415                 420

Ser Ser Pro Thr Thr Arg Pro Pro Ile Tyr
                425                 430

Phe Arg Lys Lys Arg Ser Ile Leu Trp Arg
                435                 440

Glu Gly Asp Met Phe Pro Phe Leu Asp Gly
                445                 450

Leu Ile Asn Ala Pro Ile Asp Phe Asp Pro
                455                 460

Val Pro Asn Thr Lys Thr Ile Phe Asp Glu
                465                 470

Ser Ser Ser Ser Gly Ala Ser Ala Glu Glu
                475                 480

Asp Gln His Ala Ser Pro Asn Ile Ser Leu
                485                 490

Thr Leu Ser Tyr Phe Pro Asn Ile Asn Glu
                495                 500

Asn Thr Ala Tyr Ser Gly Glu Asn Glu Asn
                505                 510

Asp Cys Asp Ala Glu Leu Arg Ile Trp Ser
                515                 520

Val Gln Glu Asp Asp Leu Ala Ala Gly Leu
                525                 530

Ser Trp Ile Pro Phe Phe Gly Pro Gly Ile
                535                 540

Glu Gly Leu Tyr Thr Ala Val Leu Ile Lys
                545                 550

Asn Gln Asn Asn Leu Val Cys Arg Leu Arg
                555                 560

Arg Leu Ala Asn Gln Thr Ala Lys Ser Leu
                565                 570

Glu Leu Leu Leu Arg Val Thr Thr Glu Glu
                575                 580

Arg Thr Phe Ser Leu Ile Asn Arg His Ala
                585                 590

Ile Asp Phe Leu Leu Thr Arg Trp Gly Gly
                595                 600

Thr Cys Lys Val Leu Gly Pro Asp Cys Cys
                605                 610

Ile Gly Ile Glu Asp Leu Ser Lys Asn Ile
                615                 620

Ser Glu Gln Ile Asp Gln Ile Lys Lys Asp
                625                 630

Glu Gln Lys Glu Gly Thr Gly Trp Gly Leu
                635                 640

Gly Gly Lys Trp Trp Thr Ser Asp Trp Gly
                645                 650

Val Leu Thr Asn Leu Gly Ile Leu Leu Leu
                655                 660

Leu Ser Ile Ala Val Leu Ile Ala Leu Ser
                665                 670

Cys Ile Cys Arg Ile Phe Thr Lys Tyr Ile
                675                 680
```

Gly

<210> SEQ ID NO 9
<211> LENGTH: 2051
<212> TYPE: DNA
<213> ORGANISM: Marburg virus strain Musoke
<220> FEATURE:
<223> OTHER INFORMATION: chimeric molecule between Marburg virus
      Glycoprotein 1 and Marburg virus Glycoprotein 2

<400> SEQUENCE: 9

| | | | | | |
|---|---|---|---|---|---|
| aagcttaaca | tgaagaccac | atgtttcctt | atcagtctta | tcttaattca | 50 |
| agggacaaaa | aatctcccca | ttttagagat | agctagtaat | aatcaacccc | 100 |
| aaaatgtgga | ttcggtatgc | tccggaactc | tccagaagac | agaagacgtc | 150 |
| catctgatgg | gattcacact | gagtgggcaa | aaagttgctg | attccccttt | 200 |
| ggaggcatcc | aagcgatggg | ctttcaggac | aggtgtacct | cccaagaatg | 250 |
| ttgagtacac | agagggggag | gaagccaaaa | catgctacaa | tataagtgta | 300 |
| acggatccct | ctggaaaatc | cttgctgtta | gatcctccta | ccaacatccg | 350 |
| tgactatccg | aaatgcaaaa | ctatccatca | tattcaaggt | caaaaccctc | 400 |
| atgcacaggg | gatcgccctt | catttatggg | gagcattttt | tctgtatgat | 450 |
| cgcattatgt | accgaggcaa | agtcttcact | gaagggaaca | tagcagctat | 500 |
| gattgtcaat | aagacagtgc | acaaaatgat | tttctcgcgg | caaggacaag | 550 |
| ggtaccgtca | tatgaatctg | acttctacta | ataaatattg | gacaagtagt | 600 |
| aacggaacgc | aaacgaatga | cactggatgt | ttcggcgctc | ttcaagaata | 650 |
| caattctaca | aagaaccaaa | catgtgctcc | gtccaaaata | cctccaccac | 700 |
| tgcccacagc | ccgtccggag | atcaaactca | caagcacccc | aactgatgcc | 750 |
| accaaactca | ataccacgga | cccaagcagt | gatgatgagg | acctcgcaac | 800 |
| atccggctca | gggtccggag | aacgagaacc | ccacacaact | tctgatgcgg | 850 |
| tcaccaagca | agggctttca | tcaacaatgc | cacccactcc | ctcaccacaa | 900 |
| ccaagcacgc | cacagcaagg | aggaaacaac | acaaaccatt | cccaagatgc | 950 |
| tgtgactgaa | ctagacaaaa | ataacacaac | tgcacaaccg | tccatgcccc | 1000 |
| ctcataacac | taccacaatc | tctactaaca | cacctccaa | acacaacttc | 1050 |
| agcactctct | ctgcaccatt | acaaaacacc | accaatgaca | cacacagag | 1100 |
| cacaatcact | gaaaatgagc | aaaccagtgc | ccctcgata | caaccctgc | 1150 |
| ctccaacggg | aaatcccacc | acagcaaaga | gcaccagcag | caaaaaaggc | 1200 |
| cccgccacaa | cggcaccaaa | cacgacaaat | gagcatttca | ccagtcctcc | 1250 |
| ccccacccc | agctcgactg | cacaacatct | tgtatattc | agaagaaagc | 1300 |
| gatcgatcct | ctggagggaa | ggcgacatgt | tccctttct | ggatggggtta | 1350 |
| ataaatgctc | caattgattt | tgacccagtt | ccaaatacaa | aaacaatctt | 1400 |
| tgatgaatcc | tctagttctg | gtgcctcggc | tgaggaagat | caacatgcct | 1450 |
| cccccaatat | tagtttaact | ttatcttatt | ttcctaatat | aaatgagaac | 1500 |
| actgcctact | ctggagaaaa | tgagaatgat | tgtgatgcag | agttaagaat | 1550 |
| ttggagcgtt | caggaggatg | acctggccgc | agggctcagt | tggataccgt | 1600 |
| tttttggccc | tggaattgaa | ggactttaca | ctgctgtttt | aattaaaaat | 1650 |

-continued

```
caaaacaatt tggtctgcag gttgaggcgt ctagccaatc aaactgccaa      1700
atccttggaa ctcttattga gagtcacaac tgaggaaaga acattctcct      1750
taatcaatag acatgctatt gactttctac tcacaagatg gggaggaaca      1800
tgcaaagtgc ttggacctga ttgttgcatc gggatagaag acttgtccaa      1850
aaatatttca gagcaaattg accaaattaa aaaggacgaa caaaaagagg      1900
ggactggttg gggtctgggt ggtaaatggt ggacatccga ctggggtgtt      1950
cttactaact tgggcatttt gctactatta tccatagctg tcttgattgc      2000
tctatcctgt atttgtcgta tctttactaa atatatcgga taacggaatt      2050
c                                                          2051
```

<210> SEQ ID NO 10
<211> LENGTH: 681
<212> TYPE: PRT
<213> ORGANISM: Marburg virus strain Musoke
<220> FEATURE:
<223> OTHER INFORMATION: chimeric molecule between Marburg virus Glycoprotein 1 and Marburg virus Glycoprotein 2

<400> SEQUENCE: 10

```
Met Lys Thr Thr Cys Phe Leu Ile Ser Leu
 1               5                  10

Ile Leu Ile Gln Gly Thr Lys Asn Leu Pro
            15                  20

Ile Leu Glu Ile Ala Ser Asn Asn Gln Pro
            25                  30

Gln Asn Val Asp Ser Val Cys Ser Gly Thr
            35                  40

Leu Gln Lys Thr Glu Asp Val His Leu Met
            45                  50

Gly Phe Thr Leu Ser Gly Gln Lys Val Ala
            55                  60

Asp Ser Pro Leu Glu Ala Ser Lys Arg Trp
            65                  70

Ala Phe Arg Thr Gly Val Pro Pro Lys Asn
            75                  80

Val Glu Tyr Thr Glu Gly Glu Glu Ala Lys
            85                  90

Thr Cys Tyr Asn Ile Ser Val Thr Asp Pro
            95                 100

Ser Gly Lys Ser Leu Leu Leu Asp Pro Pro
           105                 110

Thr Asn Ile Arg Asp Tyr Pro Lys Cys Lys
           115                 120

Thr Ile His His Ile Gln Gly Gln Asn Pro
           125                 130

His Ala Gln Gly Ile Ala Leu His Leu Trp
           135                 140

Gly Ala Phe Phe Leu Tyr Asp Arg Ile Ala
           145                 150

Ser Thr Thr Met Tyr Arg Gly Lys Val Phe
           155                 160

Thr Glu Gly Asn Ile Ala Ala Met Ile Val
```

```
                        165                 170
Asn Lys Thr Val His Lys Met Ile Phe Ser
            175                 180

Arg Gln Gly Gln Gly Tyr Arg His Met Asn
            185                 190

Leu Thr Ser Thr Asn Lys Tyr Trp Thr Ser
            195                 200

Ser Asn Gly Thr Gln Thr Asn Asp Thr Gly
            205                 210

Cys Phe Gly Ala Leu Gln Glu Tyr Asn Ser
            215                 220

Thr Lys Asn Gln Thr Cys Ala Pro Ser Lys
            225                 230

Ile Pro Pro Pro Leu Pro Thr Ala Arg Pro
            235                 240

Glu Ile Lys Leu Thr Ser Thr Pro Thr Asp
            245                 250

Ala Thr Lys Leu Asn Thr Thr Asp Pro Ser
            255                 260

Ser Asp Asp Glu Asp Leu Ala Thr Ser Gly
            265                 270

Ser Gly Ser Gly Glu Arg Glu Pro His Thr
            275                 280

Thr Ser Asp Ala Val Thr Lys Gln Gly Leu
            285                 290

Ser Ser Thr Met Pro Pro Thr Pro Ser Pro
            295                 300

Gln Pro Ser Thr Pro Gln Gln Gly Gly Asn
            305                 310

Asn Thr Asn His Ser Gln Asp Ala Val Thr
            315                 320

Glu Leu Asp Lys Asn Asn Thr Thr Ala Gln
            325                 330

Pro Ser Met Pro Pro His Asn Thr Thr Thr
            335                 340

Ile Ser Thr Asn Asn Thr Ser Lys His Asn
            345                 350

Phe Ser Thr Leu Ser Ala Pro Leu Gln Asn
            355                 360

Thr Thr Asn Asp Asn Thr Gln Ser Thr Ile
            365                 370

Thr Glu Asn Glu Gln Thr Ser Ala Pro Ser
            375                 380

Ile Thr Thr Leu Pro Pro Thr Gly Asn Pro
            385                 390

Thr Thr Ala Lys Ser Thr Ser Ser Lys Lys
            395                 400

Gly Pro Ala Thr Thr Ala Pro Asn Thr Thr
            405                 410

Asn Glu His Phe Thr Ser Pro Pro Pro Thr
            415                 420

Pro Ser Ser Thr Ala Gln His Leu Val Tyr
            425                 430
```

```
Phe Arg Arg Lys Arg Ser Ile Leu Trp Arg
            435                 440

Glu Gly Asp Met Phe Pro Phe Leu Asp Gly
            445                 450

Leu Ile Asn Ala Pro Ile Asp Phe Asp Pro
            455                 460

Val Pro Asn Thr Lys Thr Ile Phe Asp Glu
            465                 470

Ser Ser Ser Ser Gly Ala Ser Ala Glu Glu
            475                 480

Asp Gln His Ala Ser Pro Asn Ile Ser Leu
            485                 490

Thr Leu Ser Tyr Phe Pro Asn Ile Asn Glu
            495                 500

Asn Thr Ala Tyr Ser Gly Glu Asn Glu Asn
            505                 510

Asp Cys Asp Ala Glu Leu Arg Ile Trp Ser
            515                 520

Val Gln Glu Asp Asp Leu Ala Ala Gly Leu
            525                 530

Ser Trp Ile Pro Phe Phe Gly Pro Gly Ile
            535                 540

Glu Gly Leu Tyr Thr Ala Val Leu Ile Lys
            545                 550

Asn Gln Asn Asn Leu Val Cys Arg Leu Arg
            555                 560

Arg Leu Ala Asn Gln Thr Ala Lys Ser Leu
            565                 570

Glu Leu Leu Leu Arg Val Thr Thr Glu Glu
            575                 580

Arg Thr Phe Ser Leu Ile Asn Arg His Ala
            585                 590

Ile Asp Phe Leu Leu Thr Arg Trp Gly Gly
            595                 600

Thr Cys Lys Val Leu Gly Pro Asp Cys Cys
            605                 610

Ile Gly Ile Glu Asp Leu Ser Lys Asn Ile
            615                 620

Ser Glu Gln Ile Asp Gln Ile Lys Lys Asp
            625                 630

Glu Gln Lys Glu Gly Thr Gly Trp Gly Leu
            635                 640

Gly Gly Lys Trp Trp Thr Ser Asp Trp Gly
            645                 650

Val Leu Thr Asn Leu Gly Ile Leu Leu Leu
            655                 660

Leu Ser Ile Ala Val Leu Ile Ala Leu Ser
            665                 670

Cys Ile Cys Arg Ile Phe Thr Lys Tyr Ile
            675                 680

Gly
```

<210> SEQ ID NO 11
<211> LENGTH: 2039
<212> TYPE: DNA
<213> ORGANISM: Ebola virus Zaire strain
<220> FEATURE:
<223> OTHER INFORMATION: chimeric molecule between Ebola virus
      Glycoprotein 1 and Ebola virus Glycoprotein 2

<400> SEQUENCE: 11

| | | | | |
|---|---|---|---|---|
| atgggcgtta | caggaatatt | gcagttacct | cgtgatcgat | tcaagaggac | 50 |
| atcattcttt | ctttgggtaa | ttatcctttt | ccaaagaaca | ttttccatcc | 100 |
| cacttggagt | catccacaat | agcacattac | aggttagtga | tgtcgacaaa | 150 |
| ctagtttgtc | gtgacaaact | gtcatccaca | aatcaattga | gatcagttgg | 200 |
| actgaatctc | gaagggaatg | gagtggcaac | tgacgtgcca | tctgcaacta | 250 |
| aaagatgggg | cttcaggtcc | ggtgtcccac | caaaggtggt | caattatgaa | 300 |
| gctggtgaat | gggctgaaaa | ctgctacaat | cttgaaatca | aaaaacctga | 350 |
| cgggagtgag | tgtctaccag | cagcgccaga | cgggattcgg | gcttcccccc | 400 |
| ggtgccggta | tgtgcacaaa | gtatcaggaa | cgggaccgtg | tgccggagac | 450 |
| tttgccttcc | ataaagaggg | tgctttcttc | ctgtatgatc | gacttgcttc | 500 |
| cacagttatc | taccgaggaa | cgactttcgc | tgaaggtgtc | gttgcatttc | 550 |
| tgatactgcc | ccaagctaag | aaggacttct | tcagctcaca | ccccttgaga | 600 |
| gagccggtca | tgcaacggaa | ggacccgtct | agtggctact | attctaccac | 650 |
| aattagatat | caggctaccg | gttttggaac | caatgagaca | gagtacttgt | 700 |
| tcgaggttga | caatttgacc | tacgtccaac | ttgaatcaag | attcacacca | 750 |
| cagtttctgc | tccagctgaa | tgagacaata | tatacaagtg | ggaaaaggag | 800 |
| caataccacg | ggaaaactaa | tttggaaggt | caaccccgaa | attgatacaa | 850 |
| caatcgggga | gtgggccttc | tgggaaacta | aaaaaaacct | cactagaaaa | 900 |
| attcgcagtg | aagagttgtc | tttcacagtt | gtatcaaacg | gagccaaaaa | 950 |
| catcagtggt | cagagtccgg | cgcgaacttc | ttccgaccca | gggaccaaca | 1000 |
| caacaactga | agaccacaaa | atcatggctt | cagaaaattc | ctctgcaatg | 1050 |
| gttcaagtgc | acagtcaagg | aagggaagct | gcagtgtcgc | atctaacaac | 1100 |
| ccttgccaca | atctccacga | gtccccaatc | cctcacaacc | aaaccaggtc | 1150 |
| cggacaacag | cacccataat | acaccgtgt | ataaacttga | catctctgag | 1200 |
| gcaactcaag | ttgaacaaca | tcaccgcaga | acagacaacg | acagcacagc | 1250 |
| ctccgacact | ccctctgcca | cgaccgcagc | cggaccccca | aaagcagaga | 1300 |
| acaccaacac | gagcaagagc | actgacttcc | tggaccccgc | caccacaaca | 1350 |
| agtccccaaa | accacagcga | gaccgctggc | aacaacaaca | ctcatcacca | 1400 |
| agataccgga | gaagagagtg | ccagcagcgg | gaagctaggc | ttaattacca | 1450 |
| atactattgc | tggagtcgca | ggactgatca | caggcgggaa | gaagaactcga | 1500 |
| cgatcggcaa | ttgtcaatgc | tcaacccaaa | tgcaacccta | atttacatta | 1550 |
| ctggactact | caggatgaag | gtgctgcaat | cggactggcc | tggataccat | 1600 |
| atttcgggcc | agcagccgag | ggaatttaca | tagagggctt | aatgcacaat | 1650 |
| caagatggtt | taatctgtgg | gttgagacag | ctggccaacg | agacgactca | 1700 |
| agctcttcaa | ctgttcctga | gagccacaac | tgagctacgc | accttttcaa | 1750 |

-continued

```
tcctcaaccg taaggcaatt gatttcttgc tgcagcgatg gggcggcaca       1800
tgccacattc tgggaccgga ctgctgtatc gaaccacatg attggaccaa       1850
gaacataaca gacaaaattg atcagattat tcatgatttt gttgataaaa       1900
cccttccgga ccaggggac aatgacaatt ggtggacagg atggagacaa        1950
tggataccgg caggtattgg agttacaggc gttataattg cagttatcgc       2000
tttattctgt atatgcaaat ttgtctttta gttgaattc                   2039
```

<210> SEQ ID NO 12
<211> LENGTH: 676
<212> TYPE: PRT
<213> ORGANISM: Ebola virus Zaire strain
<220> FEATURE:
<223> OTHER INFORMATION: chimeric molecule between Ebola virus
      Glycoprotein 1 and Ebola virus Glycoprotein 2

<400> SEQUENCE: 12

```
Met Gly Val Thr Gly Ile Leu Gln Leu Pro
  1               5                  10

Arg Asp Arg Phe Lys Arg Thr Ser Phe Phe
                 15                  20

Leu Trp Val Ile Ile Leu Phe Gln Arg Thr
                 25                  30

Phe Ser Ile Pro Leu Gly Val Ile His Asn
                 35                  40

Ser Thr Leu Gln Val Ser Asp Val Asp Lys
                 45                  50

Leu Val Cys Arg Asp Lys Leu Ser Ser Thr
                 55                  60

Asn Gln Leu Arg Ser Val Gly Leu Asn Leu
                 65                  70

Glu Gly Asn Gly Val Ala Thr Asp Val Pro
                 75                  80

Ser Ala Thr Lys Arg Trp Gly Phe Arg Ser
                 85                  90

Gly Val Pro Pro Lys Val Val Asn Tyr Glu
                 95                 100

Ala Gly Glu Trp Ala Glu Asn Cys Tyr Asn
                105                 110

Leu Glu Ile Lys Lys Pro Asp Gly Ser Glu
                115                 120

Cys Leu Pro Ala Ala Pro Asp Gly Ile Arg
                125                 130

Gly Phe Pro Arg Cys Arg Tyr Val His Lys
                135                 140

Val Ser Gly Thr Gly Pro Cys Ala Gly Asp
                145                 150

Phe Ala Phe His Lys Glu Gly Ala Phe Phe
                155                 160

Leu Tyr Asp Arg Leu Ala Ser Thr Val Ile
                165                 170

Tyr Arg Gly Thr Thr Phe Ala Glu Gly Val
                175                 180

Val Ala Phe Leu Ile Leu Pro Gln Ala Lys
```

```
                    185                 190
Lys Asp Phe Phe Ser Ser His Pro Leu Arg
                    195                 200

Glu Pro Val Asn Ala Thr Glu Asp Pro Ser
                    205                 210

Ser Gly Tyr Tyr Ser Thr Thr Ile Arg Tyr
                    215                 220

Gln Ala Thr Gly Phe Gly Thr Asn Glu Thr
                    225                 230

Glu Tyr Leu Phe Glu Val Asp Asn Leu Thr
                    235                 240

Tyr Val Gln Leu Glu Ser Arg Phe Thr Pro
                    245                 250

Gln Phe Leu Leu Gln Leu Asn Glu Thr Ile
                    255                 260

Tyr Thr Ser Gly Lys Arg Ser Asn Thr Thr
                    265                 270

Gly Lys Leu Ile Trp Lys Val Asn Pro Glu
                    275                 280

Ile Asp Thr Thr Ile Gly Glu Trp Ala Phe
                    285                 290

Trp Glu Thr Lys Lys Asn Leu Thr Arg Lys
                    295                 300

Ile Arg Ser Glu Glu Leu Ser Phe Thr Val
                    305                 310

Val Ser Asn Gly Ala Lys Asn Ile Ser Gly
                    315                 320

Gln Ser Pro Ala Arg Thr Ser Ser Asp Pro
                    325                 330

Gly Thr Asn Thr Thr Thr Glu Asp His Lys
                    335                 340

Ile Met Ala Ser Glu Asn Ser Ser Ala Met
                    345                 350

Val Gln Val His Ser Gln Gly Arg Glu Ala
                    355                 360

Ala Val Ser His Leu Thr Thr Leu Ala Thr
                    365                 370

Ile Ser Thr Ser Pro Gln Ser Leu Thr Thr
                    375                 380

Lys Pro Gly Pro Asp Asn Ser Thr His Asn
                    385                 390

Thr Pro Val Tyr Lys Leu Asp Ile Ser Glu
                    395                 400

Ala Thr Gln Val Glu Gln His His Arg Arg
                    405                 410

Thr Asp Asn Asp Ser Thr Ala Ser Asp Thr
                    415                 420

Pro Ser Ala Thr Thr Ala Ala Gly Pro Pro
                    425                 430

Lys Ala Glu Asn Thr Asn Thr Ser Lys Ser
                    435                 440

Thr Asp Phe Leu Asp Pro Ala Thr Thr Thr
                    445                 450
```

Ser Pro Gln Asn His Ser Glu Thr Ala Gly
            455                 460

Asn Asn Asn Thr His His Gln Asp Thr Gly
            465                 470

Glu Glu Ser Ala Ser Ser Gly Lys Leu Gly
            475                 480

Leu Ile Thr Asn Thr Ile Ala Gly Val Ala
            485                 490

Gly Leu Ile Thr Gly Gly Arg Arg Thr Arg
            495                 500

Arg Ser Ala Ile Val Asn Ala Gln Pro Lys
            505                 510

Cys Asn Pro Asn Leu His Tyr Trp Thr Thr
            515                 520

Gln Asp Glu Gly Ala Ala Ile Gly Leu Ala
            525                 530

Trp Ile Pro Tyr Phe Gly Pro Ala Ala Glu
            535                 540

Gly Ile Tyr Ile Glu Gly Leu Met His Asn
            545                 550

Gln Asp Gly Leu Ile Cys Gly Leu Arg Gln
            555                 560

Leu Ala Asn Glu Thr Thr Gln Ala Leu Gln
            565                 570

Leu Phe Leu Arg Ala Thr Thr Glu Leu Arg
            575                 580

Thr Phe Ser Ile Leu Asn Arg Lys Ala Ile
            585                 590

Asp Phe Leu Leu Gln Arg Trp Gly Gly Thr
            595                 600

Cys His Ile Leu Gly Pro Asp Cys Cys Ile
            605                 610

Glu Pro His Asp Trp Thr Lys Asn Ile Thr
            615                 620

Asp Lys Ile Asp Gln Ile Ile His Asp Phe
            625                 630

Val Asp Lys Thr Leu Pro Asp Gln Gly Asp
            635                 640

Asn Asp Asn Trp Trp Thr Gly Trp Arg Gln
            645                 650

Trp Ile Pro Ala Gly Ile Gly Val Thr Gly
            655                 660

Val Ile Ile Ala Val Ile Ala Leu Phe Cys
            665                 670

Ile Cys Lys Phe Val Phe
            675

<210> SEQ ID NO 13
<211> LENGTH: 2046
<212> TYPE: DNA
<213> ORGANISM: Marburg virus strain Raven
<220> FEATURE:
<223> OTHER INFORMATION: chimeric molecule between Marburg virus
      Glycoprotein 1 and Marburg virus Glycoprotein 2

```
<400> SEQUENCE: 13
atgaagacca tatattttct gattagtctc attttaatcc aaagtataaa            50
aactctccct gttttagaaa ttgctagtaa cagccaacct caagatgtag           100
attcagtgtg ctccggaacc ctccaaaaga cagaagatgt tcatctgatg           150
ggatttacac tgagtgggca aaaagttgct gattcccctt tggaagcatc           200
taaacgatgg gctttcagga caggtgttcc tcccaagaac gttgagtata           250
cggaaggaga agaagccaaa acatgttaca atataagtgt aacagaccct           300
tctggaaaat ccttgctgct ggatcctccc agtaatatcc gcgattaccc           350
taaatgtaaa actgttcatc atattcaagg tcaaaaccct catgcacagg           400
ggattgccct ccatttgtgg ggggcatttt tcttgtatga tcgcgttgcc           450
tctacaacaa tgtaccgagg caaggtcttc actgaaggaa atatagcagc           500
tatgattgtt aataagacag ttcacagaat gattttttct aggcaaggac           550
aaggttatcg tcacatgaac ttgacctcca ccaataaata ttggacaagc           600
agcaatgaaa cgcagagaaa tgatacggga tgttttggca tcctccaaga           650
atacaactcc acaaacaatc aaacatgccc tccatctctt aaacctccat           700
ccctgcccac agtaactccg agcattcact ctacaaatac tcaaattaat           750
actgctaaat ctggaactat gaacccaagt agcgacgatg aggaccttat           800
gatttccggc tcaggatctg agaacagggg cccccacaca actcttaatg           850
tagtcactga acagaaacaa tcgtcaacaa tattgtccac tccttcacta           900
catccaagca cctcacaaca tgagcaaaac agtacgaatc cttcccgaca           950
tgctgtaact gagcacaatg gaaccgaccc aacaacacaa ccagcaacgc          1000
tcctcaacaa tactaataca actcccacct ataacactct caagtacaac          1050
ctcagtactc cttcccctcc aacccgcaac atcaccaata atgatacaca          1100
acgtgaacta gcagaaagcg aacaaaccaa tgctcagttg aacacaactc          1150
tagatccaac agaaaatccc accacaggac aagacaccaa cagcacaacc          1200
aacatcatca tgacgacatc agatataaca agcaaacacc ccacaaattc          1250
ttctccggat tctagtccga caacccgccc tcctatatac tttagaaaga          1300
aacgatcgat tttctggaaa gaaggtgata tattcccgtt tttagatggg          1350
ttaataaata ctgaaattga ttttgatcca atcccaaaca cagaaacaat          1400
ctttgatgaa tctcccagct ttaatacttc aactaatgag gaacaacaca          1450
ctcccccgaa tatcagttta actttctctt attttcctga taaaaatgga          1500
gatactgcct actctgggga aaacgagaat gattgtgatg cagagttgag          1550
gatttggagt gtgcaggagg acgatttggc ggcagggctt agctggatac          1600 catttttttgg ccctggaatc gaaggactct atactgccgg tttaatcaaa          1650
aatcagaaca atttagtttg taggttgagg cgcttagcta atcaaactgc          1700
taaatccttg gagctcttgt taagggtcac aaccgaggaa aggacatttt          1750
ccttaatcaa taggcatgca attgactttt tgcttacgag gtggggcgga          1800
acatgcaagg tgctaggacc tgattgttgc ataggaatag aagatctatc          1850
taaaaatatc tcagaacaaa tcgacaaaat cagaaaggat gaacaaaagg          1900
aggaaactgg ctggggtcta ggtggcaaat ggtggacatc tgactgggt            1950
```

```
gttctcacca atttgggcat cctgctacta ttatctatag ctgttctgat         2000
tgctctgtcc tgtatctgtc gtatcttcac taaatacatt ggatga            2046
```

<210> SEQ ID NO 14
<211> LENGTH: 681
<212> TYPE: PRT
<213> ORGANISM: Marburg virus strain Raven
<220> FEATURE:
<223> OTHER INFORMATION: chimeric molecule between Marburg virus
      Glycoprotein 1 and Marburg virus Glycoprotein 2

<400> SEQUENCE: 14

```
Met Lys Thr Ile Tyr Phe Leu Ile Ser Leu
 1               5                  10

Ile Leu Ile Gln Ser Ile Lys Thr Leu Pro
             15                  20

Val Leu Glu Ile Ala Ser Asn Ser Gln Pro
         25                  30

Gln Asp Val Asp Ser Val Cys Ser Gly Thr
         35                  40

Leu Gln Lys Thr Glu Asp Val His Leu Met
         45                  50

Gly Phe Thr Leu Ser Gly Gln Lys Val Ala
         55                  60

Asp Ser Pro Leu Glu Ala Ser Lys Arg Trp
         65                  70

Ala Phe Arg Thr Gly Val Pro Pro Lys Asn
         75                  80

Val Glu Tyr Thr Glu Gly Glu Glu Ala Lys
         85                  90

Thr Cys Tyr Asn Ile Ser Val Thr Asp Pro
         95                  100

Ser Gly Lys Ser Leu Leu Leu Asp Pro Pro
         105                 110

Ser Asn Ile Arg Asp Tyr Pro Lys Cys Lys
         115                 120

Thr Val His His Ile Gln Gly Gln Asn Pro
         125                 130

His Ala Gln Gly Ile Ala Leu His Leu Trp
         135                 140

Gly Ala Phe Phe Leu Tyr Asp Arg Val Ala
         145                 150

Ser Thr Thr Met Tyr Arg Gly Lys Val Phe
         155                 160

Thr Glu Gly Asn Ile Ala Ala Met Ile Val
         165                 170

Asn Lys Thr Val His Arg Met Ile Phe Ser
         175                 180

Arg Gln Gly Gln Gly Tyr Arg His Met Asn
         185                 190

Leu Thr Ser Thr Asn Lys Tyr Trp Thr Ser
         195                 200

Ser Asn Glu Thr Gln Arg Asn Asp Thr Gly
         205                 210
```

```
Cys Phe Gly Ile Leu Gln Glu Tyr Asn Ser
            215                 220

Thr Asn Asn Gln Thr Cys Pro Pro Ser Leu
            225                 230

Lys Pro Pro Ser Leu Pro Thr Val Thr Pro
            235                 240

Ser Ile His Ser Thr Asn Thr Gln Ile Asn
            245                 250

Thr Ala Lys Ser Gly Thr Met Asn Pro Ser
            255                 260

Ser Asp Asp Glu Asp Leu Met Ile Ser Gly
            265                 270

Ser Gly Ser Gly Glu Gln Gly Pro His Thr
            275                 280

Thr Leu Asn Val Val Thr Glu Gln Lys Gln
            285                 290

Ser Ser Thr Ile Leu Ser Thr Pro Ser Leu
            295                 300

His Pro Ser Thr Ser Gln His Glu Gln Asn
            305                 310

Ser Thr Asn Pro Ser Arg His Ala Val Thr
            315                 320

Glu His Asn Gly Thr Asp Pro Thr Thr Gln
            325                 330

Pro Ala Thr Leu Leu Asn Asn Thr Asn Thr
            335                 340

Thr Pro Thr Tyr Asn Thr Leu Lys Tyr Asn
            345                 350

Leu Ser Thr Pro Ser Pro Pro Thr Arg Asn
            355                 360

Ile Thr Asn Asn Asp Thr Gln Arg Glu Leu
            365                 370

Ala Glu Ser Glu Gln Thr Asn Ala Gln Leu
            375                 380

Asn Thr Thr Leu Asp Pro Thr Glu Asn Pro
            385                 390

Thr Thr Gly Gln Asp Thr Asn Ser Thr Thr
            395                 400

Asn Ile Ile Met Thr Thr Ser Asp Ile Thr
            405                 410

Ser Lys His Pro Thr Asn Ser Ser Pro Asp
            415                 420

Ser Ser Pro Thr Thr Arg Pro Pro Ile Tyr
            425                 430

Phe Arg Lys Lys Arg Ser Ile Phe Trp Lys
            435                 440

Glu Gly Asp Ile Phe Pro Phe Leu Asp Gly
            445                 450

Leu Ile Asn Thr Glu Ile Asp Phe Asp Pro
            455                 460

Ile Pro Asn Thr Glu Thr Ile Phe Asp Glu
            465                 470

Ser Pro Ser Phe Asn Thr Ser Thr Asn Glu
```

```
                    475                 480

Glu Gln His Thr Pro Asn Ile Ser Leu
                485                 490

Thr Phe Ser Tyr Phe Pro Asp Lys Asn Gly
                495                 500

Asp Thr Ala Tyr Ser Gly Glu Asn Glu Asn
                505                 510

Asp Cys Asp Ala Glu Leu Arg Ile Trp Ser
                515                 520

Val Gln Glu Asp Asp Leu Ala Ala Gly Leu
                525                 530

Ser Trp Ile Pro Phe Phe Gly Pro Gly Ile
                535                 540

Glu Gly Leu Tyr Thr Ala Gly Leu Ile Lys
                545                 550

Asn Gln Asn Asn Leu Val Cys Arg Leu Arg
                555                 560

Arg Leu Ala Asn Gln Thr Ala Lys Ser Leu
                565                 570

Glu Leu Leu Leu Arg Val Thr Thr Glu Glu
                575                 580

Arg Thr Phe Ser Leu Ile Asn Arg His Ala
                585                 590

Ile Asp Phe Leu Leu Thr Arg Trp Gly Gly
                595                 600

Thr Cys Lys Val Leu Gly Pro Asp Cys Cys
                605                 610

Ile Gly Ile Glu Asp Leu Ser Lys Asn Ile
                615                 620

Ser Glu Gln Ile Asp Lys Ile Arg Lys Asp
                625                 630

Glu Gln Lys Glu Glu Thr Gly Trp Gly Leu
                635                 640

Gly Gly Lys Trp Trp Thr Ser Asp Trp Gly
                645                 650

Val Leu Thr Asn Leu Gly Ile Leu Leu Leu
                655                 660

Leu Ser Ile Ala Val Leu Ile Ala Leu Ser
                665                 670

Cys Ile Cys Arg Ile Phe Thr Lys Tyr Ile
                675                 680

Gly

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
caagcttcaa tgggcgttac a                                                   21

<210> SEQ ID NO 16
<211> LENGTH: 22
```

<212> TYPE: DNA
<213> ORGANISM: Artificial Sequence
<220> FEATURE:
<223> OTHER INFORMATION: primer

<400> SEQUENCE: 16
aagcttaaca tgaagaccac at                                              22

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gacgatcggc aattgtcaat g                                               21

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
agcgatcgat cctctggag                                                  19

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gccgatcgtc gagttcttct                                                 20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
gatcgatcgc tttcttctg                                                  19

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
tgaattcaac taaaagacaa atttg                                           25

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cgaattccgt tatccgatat at                                              22

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
aagcttaaca tcaagaccac at                                              22

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
aagcttcgac atgaagacca tat                                             23

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
agcgatcgat cctctggag                                                  19

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
aacgatcgat tttctggaa                                                  19

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
gatcgatcgc tttcttctg                                                  19

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
aaatcgatcg tttctttcta aag                                             23

<210> SEQ ID NO 29
<211> LENGTH: 22
<212> TYPE: DNA
<213> ORGANISM: Artificial Sequence

```
<220> FEATURE:
<223> OTHER INFORMATION: primer

<400> SEQUENCE: 29
cgaattccgt tatccgatat at                                            22

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
cgaattctgt catccaatgt at                                            22
```